United States Patent
Dihora et al.

(10) Patent No.: US 9,732,303 B2
(45) Date of Patent: *Aug. 15, 2017

(54) MICROCAPSULES FORMED FROM PHOSPHATE ESTERS AND COMPOSITIONS CONTAINING SAME

(71) Applicant: The Procter & Gamble Company, Cincinnati, OH (US)

(72) Inventors: Jiten Odhavji Dihora, Liberty Township, OH (US); Timothy Roy Nijakowski, Mason, OH (US); Jonathan Robert Cetti, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/989,547

(22) Filed: Jan. 6, 2016

(65) Prior Publication Data
US 2017/0191001 A1 Jul. 6, 2017

(51) Int. Cl.
| | | |
|---|---|---|
| *A61K 9/50* | (2006.01) | |
| *C11B 9/00* | (2006.01) | |
| *A61Q 5/12* | (2006.01) | |
| *A61Q 13/00* | (2006.01) | |
| *A61K 8/02* | (2006.01) | |
| *A61K 8/73* | (2006.01) | |

(Continued)

(52) U.S. Cl.
CPC ............. *C11B 9/00* (2013.01); *A61K 8/0233* (2013.01); *A61K 8/55* (2013.01); *A61K 8/732* (2013.01); *A61K 8/736* (2013.01); *A61K 8/817* (2013.01); *A61K 9/1652* (2013.01); *A61K 9/5021* (2013.01); *A61Q 5/02* (2013.01); *A61Q 5/12* (2013.01); *A61Q 13/00* (2013.01); *A61Q 15/00* (2013.01); *C11D 3/505* (2013.01); *A61K 2800/592* (2013.01); *A61K 2800/652* (2013.01)

(58) Field of Classification Search
CPC ........................... A61K 9/5021; A61K 9/1652
See application file for complete search history.

(56) References Cited

U.S. PATENT DOCUMENTS

| | | |
|---|---|---|
| 4,430,239 A | 2/1984 | Wyman |
| 5,250,290 A | 10/1993 | Giacomoni et al. |

(Continued)

FOREIGN PATENT DOCUMENTS

| | | |
|---|---|---|
| EP | 0 850 564 A1 | 7/1998 |
| EP | 1 243 321 A1 | 9/2002 |

(Continued)

OTHER PUBLICATIONS

International Search Report and Written Opinion of the International Searching Authority PCT/US2017/012074, mailed Mar. 15, 2017, 15 pages.

(Continued)

*Primary Examiner* — Carlos Azpuru
(74) *Attorney, Agent, or Firm* — Kathleen Y. Carter; Carrie M. Schwartz

(57) ABSTRACT

Microcapsules can be formed of a phosphate ester and a multivalent ion. The microcapsules can encapsulate a core material having a C log P value of about 0 or greater. The phosphate ester can be lipophilic and insoluble in aqueous solutions.

20 Claims, 2 Drawing Sheets

(51) Int. Cl.
*A61K 8/81* (2006.01)
*A61K 8/55* (2006.01)
*A61Q 5/02* (2006.01)
*A61Q 15/00* (2006.01)
*C11D 3/50* (2006.01)
*A61K 9/16* (2006.01)

(56) References Cited

U.S. PATENT DOCUMENTS

| | | | |
|---|---|---|---|
| 5,931,994 | A | 8/1999 | Mateo Herrero |
| 6,242,099 | B1 | 6/2001 | Grandmontagne et al. |
| 6,248,703 | B1 | 6/2001 | Finucane et al. |
| 6,344,488 | B1 | 2/2002 | Chenite et al. |
| 6,375,968 | B1 * | 4/2002 | Quong .................. A01N 25/28 424/407 |
| 2002/0160040 | A1 | 10/2002 | Spicer et al. |
| 2004/0157761 | A1 | 8/2004 | Man et al. |
| 2005/0197276 | A1 | 9/2005 | Rigley et al. |
| 2005/0220750 | A1 | 10/2005 | Robert et al. |
| 2005/0227907 | A1 | 10/2005 | Lee et al. |
| 2005/0249805 | A1 | 11/2005 | Holsztynska |
| 2006/0094617 | A1 | 5/2006 | Price et al. |
| 2006/0263435 | A1 | 11/2006 | Davis et al. |
| 2008/0085297 | A1 | 4/2008 | Dave et al. |
| 2008/0317795 | A1 | 12/2008 | Traynor et al. |
| 2009/0047309 | A1 | 2/2009 | Maes et al. |
| 2009/0186096 | A1 | 7/2009 | Kritzman et al. |
| 2010/0112043 | A1 | 5/2010 | Takeuchi et al. |
| 2010/0203122 | A1 | 8/2010 | Weyer et al. |
| 2011/0197782 | A1 | 8/2011 | Wang et al. |
| 2012/0165410 | A1 | 6/2012 | Dodd et al. |
| 2012/0202694 | A1 | 8/2012 | Dodd et al. |
| 2012/0237578 | A1 | 9/2012 | Lei et al. |
| 2014/0072617 | A1 | 3/2014 | Dumas et al. |

FOREIGN PATENT DOCUMENTS

| | | |
|---|---|---|
| JP | 2001-97809 A | 4/2001 |
| WO | WO 93/09176 | 5/1993 |
| WO | WO 2005/084710 A2 | 9/2005 |
| WO | WO 2006/037230 A1 | 4/2006 |
| WO | WO 2007/027711 A1 | 3/2007 |
| WO | WO 2009/123764 A2 | 10/2009 |
| WO | WO 2009/155115 A2 | 12/2009 |
| WO | WO 2010/140987 A1 | 12/2010 |
| WO | WO 2014/025977 A1 | 2/2014 |
| WO | WO 2014/193908 A1 | 12/2014 |

OTHER PUBLICATIONS

International Search Report and Written Opinion of the International Searching Authority PCT/US2017/012073, mailed Mar. 20, 2017, 11 pages.
International Search Report and Written Opinion of the International Searching Authority PCT/US2017/012075, mailed Mar. 20, 2017, 14 pages.
International Search Report and Written Opinion of the International Searching Authority PCT/US2017/012076, mailed Mar. 20, 2017, 12 pages.
U.S. Appl. No. 14/989,526, filed Jan. 6, 2016, Jonathan Robert Cetti et al.
U.S. Appl. No. 14/989,589, filed Jan. 6, 2016, Jiten Odhavji DiHora et al.
U.S. Appl. No. 14/989,610, filed Jan. 6, 2016, Jiten Odhavji DiHora et al.

* cited by examiner

MICROCAPSULES FORMED FROM PHOSPHATE ESTERS AND COMPOSITIONS CONTAINING SAME

TECHNICAL FIELD

Microcapsules having shell walls formed of phosphate ester salts, and consumer products containing such microcapsules.

BACKGROUND

Microencapsulation techniques allow for the encapsulation of materials within a protective microcapsule shell. Microcapsules are known to have utility for a variety of applications such as the controlled release of a benefit agent over time and the conversion of liquids into free flowing solids. Microcapsules are also known to extend shelf life, stabilize and protect encapsulated materials, mask flavors, and protect the encapsulated contents until the microcapsule wall is ruptured, sheared, fractured, broken, or melted. However, known microcapsules suffer from poor encapsulation yields, high permeability, low compatibility with core materials, and low mechanical strength. It would therefore be advantageous to provide an improved microcapsule that provides decreased permeability and improved mechanical properties and compatibility with core materials.

SUMMARY

In accordance with one example, a microcapsule includes a core material and shell wall. The core material is miscible with a lipophilic phosphate ester. The shell wall at least partially surrounds the core material. The shell wall includes the reaction product of the lipophilic phosphate ester and a multivalent ion.

In accordance with another example, a microcapsule includes a core material encapsulated by a phosphate ester salt. The core material has a C log P value of about 0 or greater and the phosphate ester salt includes an R-group having a carbon chain length of 6 to 18 carbon atoms.

In accordance with another example, a composition includes an adjunct ingredient and one or more microcapsules. Each microcapsule includes a core material and shell wall. The core material is miscible with a lipophilic phosphate ester. The shell wall at least partially surrounds the core material. The shell wall includes the reaction product of the lipophilic phosphate ester and a multivalent ion.

DETAILED DESCRIPTION

Definitions

Figure 1:
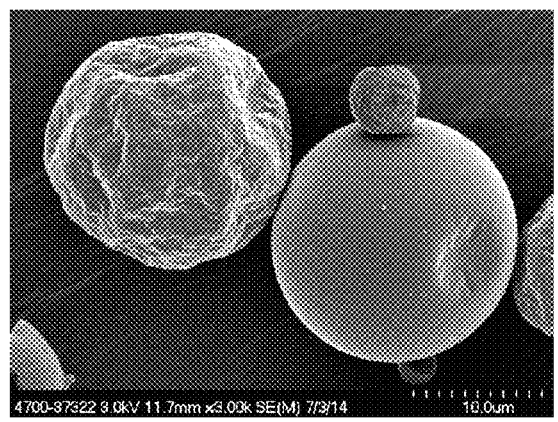
FIG. 1 depicts a cryo-SEM scan of an inventive microcapsule.

"Ambient" refers to surrounding conditions at about one atmosphere of pressure, about 50% relative humidity, and about 25° C.

"Anhydrous" refers to compositions and/or components which are substantially free of water or free of water.

"Free of" means that the stated ingredient has not been added to the antiperspirant composition. However, the stated ingredient can incidentally form as a byproduct or a reaction product of the other components of the antiperspirant composition.

As used herein "consumer product" can mean baby care, personal care, fabric and home care, family care, feminine care, health care, snack and/or beverage products or devices intended to be used or consumed in the form in which it is sold, and not intended for subsequent commercial manufacture or modification. Such consumer products can include, but are not limited to, diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, prescription pharmaceuticals, pet health and nutrition, and water purification.

As used herein, the term "cleaning composition" can include, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as foam substrates, films, and combinations thereof, bleach additives and "stain-stick" or pre-treat types, substrate-laden products such as dryer added sheets, dry and wetted wipes and pads, nonwoven substrates, and sponges; as well as sprays and mists.

As used herein, the term "personal care composition" can include, unless otherwise indicated, any personal care composition that can be applied to the keratinaceous surfaces of the body including the skin and/or hair. The personal care compositions can be, for example, formulated as bars, liquids, emulsions, shampoos, gels, powders, sticks, hair conditioners (rinse off and leave in), hair tonics, pastes, hair colorants, sprays, mousses and/or other styling products, as well as shave prep products, and devices used for shaving.

As used herein, the term "solid" includes granular, powder, bar and tablet product forms.

As used herein, the term "situs" includes paper products, fabrics, garments, hard surfaces, hair and skin.

As used herein, the articles including "a" and "an" when used in a claim, are understood to mean one or more of what is claimed or described.

As used herein, the terms "include", "includes" and "including" are meant to be non-limiting.

"Soft solid" when used with respect to a deodorant or an antiperspirant composition refers to an antiperspirant composition with a penetration force value of 700 gram force or less and utilizes an implement (like a dome on a package) for application to the underarm.

"Solid" when used with respect to a deodorant or an antiperspirant composition refers to a composition with a penetration force value of 600 gram force or more where the composition itself acts as the applicator to the underarm.

"Substantially free of" refers to about 3% or less, about 2% or less, about 1.5% or less, about 1% or less, or about 0.1% or less of a stated ingredient by weight of the antiperspirant composition.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Microcapsules

Microcapsules include a shell wall which at least partially encapsulates a core material. The shell wall can substantially encapsulate or wholly encapsulate the core material.

Microcapsules exhibiting favorable permeability and encapsulation characteristics can be formed of inorganic shell walls that include a phosphate ester material. The microcapsules can be formed through an interfacial oil-in-water polymerization process.

As can be appreciated, interfacial polymerization processes can include more than one phase. For example, the microcapsule encapsulation processes disclosed herein can include an aqueous phase, and a lipophilic phase comprising core materials, dispersed in the lipophilic phase. Upon mixing of a suitable lipophilic phase with an aqueous phase, a distinct phase boundary can occur between the two phases and an inorganic microcapsule shell wall can be formed along the phase boundary.

The lipophilic phase can include core materials to be encapsulated with a phosphate ester material. The phosphate ester material can be precipitated out of the solution to form an insoluble microcapsule shell wall around the core materials of low permeability.

Several properties are desirable in a phosphate ester to successfully form microcapsules that at least partially coat a material for use in a starch delivery vehicle. These properties include solubility in a lipophilic phase, insolubility in an aqueous phase, and stability with core materials. Solubility in a lipophilic phase and insolubility in an aqueous phase can contribute to the partitioning of the phosphate ester at an oil/water interface so that a microcapsule can form versus emulsifying into the aqueous phase which would not allow the formation of a microcapsule.

Suitable phosphate esters, and salts thereof, can include phosphate monoesters, phosphate diesters, or a mixture thereof. Chemical formulas of phosphate monoesters and phosphate diesters are depicted in Formulas I and II respectively, each of which are reproduced below:

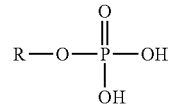

Formula I

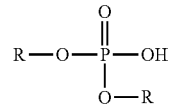

Formula II

As can be appreciated, phosphate esters can be formed from alcohols, ethoxylated alcohols, or ethoxylated phenols with the R-group of each such phosphate ester determined by the specific alcohol, ethoxylated alcohol, or ethoxylated phenol used to form the phosphate ester. The specific identity of an R-group can influence the properties of a phosphate ester compound and can, for example, determine the solubility of the phosphate ester in aqueous or lipophilic solutions and can influence whether the phosphate ester emulsifies or partitions along the phase boundary when exposed to an aqueous phase.

Phosphate esters exhibiting lipophilicity can be, for example, phosphate esters formed from certain alcohols. For example, the R-group of such phosphate alcohol esters can have a carbon chain length between about 6 carbon atoms and about 18 carbon atoms, and going further can be a $C_8$ to $C_{10}$ linear alkyl chain. As can be appreciated, such R-groups can allow a phosphate ester to be soluble in a lipophilic phase, insoluble in an aqueous phase, and partition at an oil/water interface with the R-groups arranging to face the core materials and the alcohol group(s) facing the aqueous phase. R-groups smaller than about 6 carbons in length can be insoluble in lipophilic solutions while R groups larger than about 18 carbon atoms can prevent the phosphate ester from migrating to the oil-water interface upon exposure to an aqueous solvent.

Although, phosphate esters formed of ethoxylated alcohols and ethoxylated phenols can also be lipophilic, most such phosphates esters can also be water soluble and can, as a consequence, act as a surfactant. Such surfactant-like phosphate esters can be unsuitable for a microcapsule as disclosed herein because such phosphate esters can form stable oil-in-water emulsions preventing the formation of an interfacial oil/water partition necessary for the formation of a microcapsule.

As can be appreciated, suitable phosphate esters should be unreactive with the core materials to be encapsulated. For example, a phosphate ester can be unsuitable if it chemically bonds to the core materials, causes an acid/base reaction with the core materials, causes precipitation of the core materials, or otherwise negatively affects the core materials. Examples of suitable phosphate esters that do not react with the core materials can include phosphate esters having a low acid value such as phosphate esters having an acid value below about 950 mg KOH/g, and phosphate esters having an acid value between about 190 mg KOH/g and about 450 mg KOH/g.

As noted herein, suitable phosphate esters can include phosphate monoesters, phosphate diesters, or mixtures thereof. For example, the phosphate esters can include a 1:1 ratio of phosphate monoesters and phosphate diesters. It can be advantageous to include relatively larger ratios of a phosphate diester in comparison to phosphate monoester, or to include only a phosphate diester. As can be appreciated, a phosphate diester can exhibit lower acidity than a comparable phosphate monoester and can also exhibit a higher crosslinking density since the single crosslinking site is more likely to be used for crosslinking. Exemplary phosphate esters can include hexadecyl phosphate, heptyl nonyl phosphate, octyl phosphate, and combinations thereof.

The core materials of a microcapsule as disclosed herein can vary widely. Generally, suitable core materials can be selected from any material that is miscible with the selected phosphate esters. Advantageously however, phosphate esters can be miscible with both polar and non-polar materials which can allow for a wider variety of core materials to be encapsulated than with other known microencapsulation architectures. The ability to encapsulate both polar and non-polar compounds can also eliminate the need to use a partitioning modifier to modify the polarity of the core materials. For example, menthol can be encapsulated using certain microencapsulation processes disclosed herein despite being a polar compound. Generally, a suitable core material can instead be selected on the basis of its C log P value which generally indicates lipophilicity of a compound. Suitable core materials can have a C log P value of about 0 or greater, a C log P value of about 0 to about 5; a C log P value of about 1 to about 5, or a C log P value of about 3 to about 4.5.

Illustrative examples of core materials that can be encapsulated can include, but are not limited to, perfumes; brighteners; insect repellants; silicones; waxes; flavors; vitamins; fabric softening agents; skin care agents; enzymes; probiotics; dye polymer conjugates; dye clay conjugates; perfume delivery systems; odor masking agents, odor absorbers; sensates, pheromones; anti-bacterial agents; dyes; pigments; bleaches; flavorants; sweeteners; pharmaceuticals; fertilizers; herbicides and mixtures thereof.

As discussed above, the core material can be a perfume oil. As can be appreciated, encapsulation of a perfume oil can allow for products and compositions including the microcapsules to have a controlled release of the perfume oil. The perfume oil can both slowly release over time due to degradation of the microcapsules but can also be desirably released in greater quantities during activities that cause rupturing of the microcapsules. For example, an antiperspirant composition including microcapsules as disclosed herein can provide a continuous release of perfume oil throughout the day and can release larger doses of perfume during physical activities that cause rupturing of the microcapsules due to, for example, physical shear forces and elevated heat. Examples of suitable perfume oils, and their C log P values, are depicted in Table 1.

TABLE 1

| Perfume Oils | CAS Number | ClogP Value | Boiling Point, (° C.) |
|---|---|---|---|
| 3,6-Nonadien-1-ol | 53046-97-2 | 2.5 | 213 |
| Allyl Caproate | 123-68-2 | 3.0 | 198 |
| Allyl Heptoate | 142-19-8 | 3.6 | 216 |
| Beta Gamma Hexenol | 928-96-1 | 1.3 | 155 |
| Cis 3 Hexenyl Acetate | 3681-71-8 | 2.2 | 167 |
| Cis-6-Nonen-1-OL FCC | 35854-86-5 | 2.7 | 214 |

TABLE 1-continued

| Perfume Oils | CAS Number | ClogP Value | Boiling Point, (° C.) |
|---|---|---|---|
| Cyclo Galbanate | 68901-15-5 | 2.5 | 273 |
| Cymal | 103-95-7 | 3.6 | 290 |
| Dihydro Myrcenol | 18479-58-8 | 3.1 | 195 |
| Dimethyl Benzyl Carbinyl Butyrate | 10094-34-5 | 4.1 | 270 |
| Ethyl 2 Methyl Pentanoate | 39255-32-8 | 2.6 | 157 |
| Ethyl Acetoacetate | 141-97-9 | 0.2 | 179 |
| Ethyl Caproate FCC | 123-66-0 | 2.6 | 165 |
| Ethyl Maltol | 4940-11-8 | 0.2 | 274 |
| Ethyl Oenanthate | 106-30-9 | 3.2 | 183 |
| Ethyl-2-Methyl Butyrate | 7452-79-1 | 1.9 | 133 |
| Florhydral | 125109-85-5 | 3.6 | 295 |
| Hexamethylindanopyran | 1222-05-5 | 5.4 | 398 |
| Gamma Decalactone | 706-14-9 | 3.2 | 211 |
| Hexyl Acetate | 142-92-7 | 2.6 | 165 |
| Ionone Beta | 14901-07-6 | 4.0 | 267 |
| Jasmolactone | 32764-98-0 | 2.4 | 219 |
| Liffarome | 67633-96-9 | 2.1 | 167 |
| Ligustral Or Triplal | 68039-49-6 | 1.8 | 199 |
| Linalool | 78-70-6 | 2.4 | 204 |
| Melonal | 106-72-9 | 2.1 | 182 |
| Nectaryl | 95962-14-4 | 4.2 | 319 |
| Para Hydroxy Phenyl Butanone | 5471-51-2 | 1.6 | 294 |
| Pino Acetaldehyde | 33885-51-7 | 3.0 | 261 |
| Prenyl Acetate | 1191-16-8 | 1.1 | 145 |
| Thesaron | 22471-55-2 | 3.8 | 216 |
| Undecalactone | 104-67-6 | 3.8 | 228 |
| Undecavertol | 81782-77-6 | 3.1 | 242 |
| Verdox | 88-41-5 | 3.9 | 223 |
| Verdural B Extra | 41519-23-7 | 3.2 | 193 |

A lipophilic phase can contain the core material and the phosphate ester. The core material can be a minor or major constituent of the lipophilic phase. For example, the core materials can form about 0.01% to about 99%, by weight of the lipophilic phase, about 40% to about 95% by weight of the lipophilic phase, or from about 60% to about 90% by weight of the lipophilic phase. The phosphate ester can be, for example, from about 2% to about 20%, by weight of the lipophilic phase, or from about 2% to about 12%, by weight of the lipophilic phase.

The core materials can be encapsulated within an insoluble shell wall formed by precipitation of the phosphate ester with a multivalent ion. A multivalent ion can reside in an aqueous phase. As can be appreciated, upon addition of the lipophilic phase to an aqueous solution, small droplets of the lipophilic phase can form in the aqueous phase with phosphate esters arranged at the oil-water phase boundary of each droplet. Multivalent ions present in the aqueous phase can then cause precipitation of the phosphate ester. The core materials can have very low solubility with phosphate ester salts leading to a microcapsule of very low permeability.

A variety of suitable multivalent ions can be included in an aqueous phase. For example, calcium chloride, aluminum sulfate, aluminum sulfate, chitosan, Polyethylenimine ("PEI") and polydiallyldimethylammonium chloride ("polyDADMAC") are non-limiting examples of suitable multivalent ions that can cause precipitation of a phosphate ester. A multivalent ion may be present in an amount of about 1% to about 5%, by weight of the aqueous phase.

Starch or a modified-starch such as octenylsuccinic acid anhydride ("OSAN") modified starch, can be included in an aqueous phase. Starches suitable for use can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch, and mixtures thereof. Modified starches may be particularly suitable, and these include hydrolyzed starch, acid thinned starch, starch having hydrophobic groups, such as starch esters of long chain hydrocarbons (C5 or greater), starch acetates, starch octenyl succinate and mixtures thereof. Starch esters, particularly starch octenyl succinates are especially preferred. Starch can be present in the second aqueous phase in an amount of about 20% to about 70%, by weight of the second aqueous phase.

Starch can provide various improvements to the microcapsules as disclosed herein. For example, starch can act as a strengthening component of a microcapsule shell wall, can act as a crosslinking agent to improve the strength of a microcapsule, and can act as a dehydrating agent to remove water after formation of a microcapsule.

When included, starch can be included in a separate aqueous phase from the multivalent ion aqueous phase. An aqueous phase including starch can be first mixed with a lipophilic phase before addition of the multivalent ion aqueous phase. Upon mixing of the starch phase and lipophilic phase, a matrix of starch can encapsulate the lipophilic droplets formed of phosphate ester and the core materials. Later addition of the multivalent ion aqueous phase can then cause precipitation of the phosphate ester and formation of the low permeability inorganic shell wall.

After formation of the microcapsules, they can be dried and converted to a powder through industry standard processes. For example, microcapsules can be quickly dried using a suitable spray drying apparatus. Drying of the microcapsules can allow for easier incorporation into anhydrous products forms, like antiperspirants.

As can be appreciated, the permeability of microcapsules as disclosed herein can be controlled though selection and control of various processes such as, for example, selection of the wall materials, selection of the phosphate esters, and the time and temperature of the manufacturing processes. For example, a microcapsule formed using only phosphate diester compounds can exhibit less permeability than a similar microcapsule formed from a similar phosphate monoester compound due to the greater degree of crosslinking possible in the phosphate diester compound. Without being limited be theory, it is believed that the use of Polyethylenimine as a multivalent ion can lead to more fragile microcapsules due to the Lewis acid and Lewis base interactions between the Polyethylenimine and the phosphate ester. Varying these conditions can allow the microcapsules to rupture more easily upon exposure to moisture or humidity.

The microcapsules can have an average diameter of about 10 microns to about 30 microns. The microcapsules can have a narrow particle size distribution. For example, having a mean microcapsule particle size, as calculated from the volume distribution, of 18.64 µm, the size distribution of the microcapsules can have a standard deviation of 10.30 µm. The kurtosis of the same distribution can be leptokurtic with a $K_G=1.155$.

Slurry/Agglomerate

A microcapsule may be in the form of a slurry. The slurry may be combined with an adjunct ingredient to form a composition, such as, for example, a consumer product.

A slurry can contain one or more carriers selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

A slurry can include one or more processing aids selected from the group consisting of water, aggregate inhibiting materials such as divalent salts, particle suspending polymers, and mixtures thereof. Examples of aggregate inhibiting materials can include salts that can have a charge-shielding effect around the particle, such as magnesium chloride, calcium chloride, magnesium bromide, magnesium sulfate, and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

A slurry can contain one or more deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinylamine and poivyinylalcohol oligomers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimine, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

Consumer Products

Microcapsules can be incorporated into a composition comprising an adjunct ingredient.

Antiperspirant/Deodorant Composition

For example, the microcapsules may be incorporated into a deodorant or antiperspirant composition. Adjunct ingredients for a deodorant or antiperspirant can include, for example, a deodorant active, an antiperspirant active, a carrier, or a combination thereof. Antiperspirant and deodorant compositions can be, for example, a soft solid, a solid, or an aerosol. The composition can be anhydrous.

Antiperspirant Active

The compositions can include an antiperspirant active suitable for application to human skin. The concentration of the antiperspirant active in the antiperspirant composition should be sufficient to provide the desired enhanced wetness protection. For example, the active can be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents.

An antiperspirant active can include any compound, composition, or other material having antiperspirant activity.

Such actives can include astringent metallic salts, like inorganic and organic salts of aluminum, zirconium and zinc, as well as mixtures thereof. For example, the antiperspirant active can include zirconium-containing salts or materials, such as zirconyl oxyhalides, zirconyl hydroxyhalides, and mixtures thereof; and/or aluminum-containing salts such as, for example, aluminum halides, aluminum chlorohydrate, aluminum hydroxyhalides, and mixtures thereof.

1. Aluminum Salts

Aluminum salts useful herein can include those that conform to the formula:

$$Al_2(OH)_aCl_b \cdot xH_2O$$

wherein a is from about 2 to about 5; the sum of a and b is about 6; x is from about 1 to about 6; where a, b, and x can have non-integer values. For example, aluminum chlorohydroxides referred to as "⅚ basic chlorohydroxide," wherein a is about 5 and "⅔ basic chlorohydroxide", wherein a=4 can be used.

A general description of these aluminum salts can be found in *Antiperspirants and Deodorants*, Cosmetic Science and Technology Series Vol. 20, $2^{nd}$ edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein can include those which conform to the formula:

$$ZrO(OH)_{2-a}Cl_a \cdot xH_2O$$

wherein a is from about 1.5 to about 1.87; x is from about 1 to about 7; and wherein a and x can both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Examples of two such complexes include aluminum zirconium trichlorohydrex and aluminum zirconium tetrachlorohydrex.

The antiperspirant active can comprise, for example, aluminum zirconium tetrachlorohydrex glycine; aluminum zirconium tetrachlorohydrate, aluminum zirconium pentachlorohydrate, aluminum zirconium pentachlorohydrex glycine, aluminum zirconium trichlorohydrex glycine, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

Carrier

The compositions can also include a carrier. The carrier can be present, for example, at concentrations ranging from about 10%, about 15%, about 20%, about 25%; to about 99%, about 70%, about 60%, or about 50%, by weight of the composition. Such concentrations will vary depending upon variables such as product form, desired product hardness, and selection of other ingredients in the antiperspirant composition. The carrier can be any anhydrous carrier known for use in antiperspirant or deodorant compositions or otherwise suitable for topical application to the skin. For example, anhydrous carriers can include, but are not limited to, volatile and nonvolatile fluids.

A. Volatile Fluid

The compositions can also include a volatile fluid such as a volatile silicone carrier. Volatile fluids are present, for example, at concentrations ranging from about 20% or from about 30%; to about 80%, or no about 60%, by weight of the composition. The volatile silicone of the solvent can be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone can be a cyclic silicone. The cyclic silicone can have from about 3 silicone atoms, or from about 5 silicone atoms; to about 7 silicone atoms, or to about 6 silicone atoms. For example, volatile silicones can be used which conform to the formula:

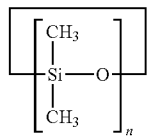

wherein n is from about 3, or from about 5; to about 7, or to about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

A non-volatile fluid can also be present, for example, at concentrations ranging from about 1%, from about 2%; to about 20%, or about 15%, by weight of the composition.

1. Non-Volatile Organic Fluids

The non-volatile organic fluid can be present at concentrations ranging from about 1%, from about 2% but no more than about 20% or no more than about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013,248 (Luebbe et al.) and U.S. Pat. No. 5,968,489 (Swaile et al.).

2. Nonvolatile Silicone Fluids

The composition can also include a non-volatile silicone fluid. The non-volatile silicone fluid can be a liquid at or below human skin temperature, or otherwise in liquid form within a antiperspirant composition, like an anhydrous antiperspirant composition, during or shortly after topical application. The concentration of the non-volatile silicone can be from about 1%, from about 2%; to about 15%, about 10%, by weight of the composition. Nonvolatile silicone fluids can include those which conform to the formula:

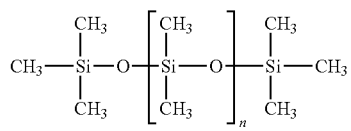

wherein n is greater than or equal to 1. These linear silicone materials can generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent can be also be used. Such solvents can be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Structurants

Antiperspirant compositions can also include a structurant to help provide the antiperspirant composition with the desired viscosity, rheology, texture and/or product hardness, or to otherwise help suspend any dispersed solids or liquids within the antiperspirant composition. The term "structurant" can include any material known or otherwise effective in providing suspending, gelling, viscosifying, solidifying, or thickening properties to the antiperspirant composition or which otherwise provide structure to the final product form. Non-limiting examples of structurants include, for example, gelling agents, polymeric or nonpolymeric agents, inorganic thickening agents, or viscosifying agents. Non-limiting examples of thickening agents include, for example, organic solids, silicone solids, crystalline or other gellants, inorganic particulates such as clays or silicas, or combinations thereof.

The concentration and type of the structurant selected for use in the antiperspirant composition can vary depending upon the desired product form, viscosity, and hardness. The thickening agents suitable for use herein, can have a concentration range from about 0.1%, about 3%, or about 5%; to about 35%, about 20%, or about 10%, by weight of the antiperspirant composition. Soft solids will often contain a lower amount of structurant than solid compositions. For example, a soft solid can contain from about 1.0% to about 9%, by weight of the composition, while a solid composition can contain from about 15% to about 25%, by weight of the antiperspirant composition, of a structurant. This is not a hard and fast rule, however, as a soft solid product with a higher structurant value can be formed by, for example, shearing the product as it is dispensed from a package.

Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Optionally, the microcapsules can be premixed with such gellants prior to incorporation into the antiperspirant composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, monsubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non-limiting examples of suitable tryiglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C (Syncrowax® available from Croda, Inc.).

Other suitable thickening agents include waxes or waxlike materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. The synthetic wax can be, for example, but not limited to, a polyethylene, a polymethylene, or a combination thereof. Some suitable polymethylenes can have a melting point from about 65° C. to about 75° C. Examples of some suitable polyethylenes include those with a melting point from about 60° C. to about 95° C. Other high melting point waxes are described in U.S. Pat. No. 4,049,792, Elsnau, issued Sep. 20, 1977.

Further structurants for use in the antiperspirant compositions can include inorganic particulate thickening agents such as clays and colloidal pyrogenic silica pigments. For example, but not limited to, colloidal pyrogenic silica pigments such as Cab-O-Sil®, a submicroscopic particulated pyrogenic silica can be used. Other known or otherwise effective inorganic particulate thickening agents that are commonly used in the art can also be used in the antiperspirant compositions described herein. Concentrations of particulate thickening agents can range, for example, from about 0.1%, about 1%, or about 5%; to about 35%, about 15%, about 10% or about 8%, by weight of the antiperspirant composition.

Clay structurants include montmorillonite clays, non-limiting examples of which include bentonites, hectorites, and colloidal magnesium aluminum silicates. These and other clays can be hydrophobically treated, and when treated will generally be used in combination with a clay activator. Non-limiting examples of suitable clay activators include propylene carbonate, ethanol, and combinations thereof. When clay activators are present, the amount of clay activator can be in a range of from about 40%, about 25%, or about 15%; to about 75%, about 60%, or about 50%, by weight of the clay.

Surfactant

The antiperspirant compositions can include a surfactant. A surfactant is generally present at a level of about 0.05% to about 5%, by weight of the antiperspirant composition, but can contain, from about 0.5% to about 5.0%; from about 1.0% to about 4%; from about 1.5% to about 3.5%; from about 1.75% to about 2.5%; about 2%, or any combination thereof. The surfactant can have a HLB range of about 2 to about 14; about 6 to about 12; about 8 to about 10; or any combination thereof. The surfactant can be free of polyoxyethylene sorbitan fatty acids. The surfactant can comprise, for example, a $C_{20-40}$ Pareth-10. Another suitable surfactant is a nonionic exthoxylated linear alcohol with a carbon chain length of 20-40. Suitable surfactants include PERFORMATHOX™ 450 ethoxylate.

Propellant

The antiperspirant composition can be in the form of an aerosol. Thus, the composition can include a propellant and be stored in a spray device. The spray device can comprise a propellant stored in one or more reservoirs of the container. The propellant may be stored in the same reservoir as an antiperspirant composition or a separate reservoir, although it is preferred that the propellant is stored within the same reservoir as the antiperspirant composition. The propellant may be present in a liquefied form that is miscible with liquid carriers of the antiperspirant composition as well as gaseous state within a head space of the reservoir. The liquid propellant and the antiperspirant composition form a mixture that travels through the container, eventually exiting the container where the liquid propellant vaporizes to from a spray. The propellant may have a concentration from about 25% to about 90%, or from about 40% to about 85%, or from about 50% to about 80%, by weight of the antiperspirant composition.

A wide variety of propellants may be used with the spray devices and antiperspirant compositions described herein, although in some embodiments the spray device is substantially free of compressed gas propellants such as nitrogen, air and carbon dioxide. Some suitable propellants may have a boiling point (at atmospheric pressure) within the range of from about −45° C. to about 5° C. Some suitable propellants may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), HF01234 (trans-1,3,3,3-tetrafluoropropene) and 152A (1,1 difluoroethane).

Other Materials

The antiperspirant compositions can also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

Other Consumer Products

In one example, a composition may include a rheology modifier, thickener and/or structurant having a high shear viscosity, at 20 sec$^{-1}$ shear rate and at 21° C., of from 1 to 7000 cps and a viscosity at low shear (0.5 sec$^{-1}$ shear rate at 21° C.) of greater than 1000 cps, or even 1000 cps to 200,000 cps. In one examples, for cleaning and treatment compositions, such rheology modifiers can impart to the aqueous liquid composition a high shear viscosity, at 20 sec$^{-1}$ and at 21° C., of from 50 to 3000 cps and a viscosity at low shear (0.5 sec$^{-1}$ shear rate at 21° C.) of greater than 1000 cps, or even 1000 cps to 200,000 cps. In one aspect, suitable rheology modifiers, thickeners and/or structurants can be selected from the group consisting of polyacrylates, polymethacrylates, polycarboxylates, polymeric gums like pectine, alginate, arabinogalactan (gum Arabic), carrageenan, gellan gum, xanthan gum and guar gum, other non-gum polysaccharides like gellan gum, and combinations of these polymeric materials, hydroxyl-containing fatty acids, fatty esters or fatty waxes, castor oil and its derivatives, hydrogenated castor oil derivatives such as hydrogenated castor oil and hydrogenated castor wax; and mixtures thereof.

The composition may be a fluid detergent that may comprise, based on total fluid detergent weight, less than about less than about 80% water, from about 60% to about 2% water, from about 45% to about 7% water, and from about 35% to about 9% water.

In one example, a composition may be a gel that can comprise, based on total gel weight, less than about 45% water, about 45% to about 2% water, from about 45% to about 7% water, from about 35% to about 9% water and may have a neat viscosity of from about 1,000 cps to about 10,000 cps or even from about 1,200 cps to about 8,000 cps. In one example, a composition can be a fluid fabric enhancer; a solid fabric enhancer; a fluid shampoo; a solid shampoo; hair conditioner; body wash; solid antiperspirant; fluid antiperspirant; solid deodorant; fluid deodorant; fluid moisturizer; solid moisturizer; fluid lotion; fluid facial cleanser; solid facial cleanser; fluid cosmetic product; solid cosmetic product; fluid hair colorant composition; solid hair colorant composition; fluid detergent; solid detergent; fluid hard surface cleaner; solid hard surface cleaner; or a unit dose detergent comprising a detergent and a water soluble film encapsulating said detergent.

The microcapsules as disclosed herein can be used in laundry detergent compositions (e.g., TIDE™), hard surface cleaners (e.g., MR CLEAN™) automatic dishwashing liquids (e.g., CASCADE™), and floor cleaners (e.g., SWIFFER™). Non-limiting examples of cleaning compositions can include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12 and a pH between about 7.5 and 10.5. Liquid dishwashing product formulations typically have a pH between about 6.8 and about 9.0. Cleaning products can have a pH of from about 7 to about 12. Techniques for controlling pH at recommended usage levels include the use of buffers, alkalis, acids, etc., and are well known to those skilled in the art.

Aspects of the disclosure can include the use of the particles in personal care compositions. As can be appreciated, personal care compositions can be applied to the skin and/or hair. The compositions can be, for example, formulated as bars, liquids, emulsions, shampoos, gels, powders, sticks, hair conditioners (rinse off and leave in), hair tonics, pastes, hair colorants, sprays, mousses and/or other styling products.

As can be appreciated, microcapsules as disclosed herein can act as a benefit delivery agent to personal care compositions and can provide continued release of a benefit agent over time. Additionally, mechanical forces and heat can cause the microcapsules to rupture and deliver the benefit agent. For example, a shampoo including a benefit delivery agent microcapsule can rupture upon combing or other mechanical movement of the hair to provide continued delivery of the benefit agent.

Personal Care Compositions

In one example, consumer products disclosed herein may be personal care compositions comprising any aspect of the microcapsules disclosed herein. Such compositions can be in solid or fluid form. Such compositions can be applied to the skin and/or hair or in other examples used to treat and/or clean a situs. The compositions can be, for example, formulated as bars, liquids, emulsions, shampoos, gels, powders, sticks, hair conditioners (rinse off and leave in), hair tonics, pastes, hair colorants, sprays, mousses and other styling products.

In one example, the microcapsules can be incorporated into a personal care composition suitable for use before, during or after hair removal. The personal care composition of the present disclosure can be used in combination with various hair removal applications (prior to, concurrently with, and/or after), including but not limited to shaving (wet or dry shaving, via electric razors, via powered or manual razors which can be reusable or disposable, and combinations thereof), epilation, electrolysis, wax or depilatories as well as energy delivery devices to help regulate hair growth. The hair removal composition can be an aerosol, such as an aerosol shave preparation which can be a foam, gel, or post foaming gel, or a non-aerosol shave preparation such as generally available in the market. In one example, the shave preparation is an emulsion which can be in the form of a cream or lotion, or the shave preparation can be a gel, which most commonly consists of polymer thickened surfactant systems.

In one example, a microcapsule can be incorporated into a shaving aid which can be incorporated into a shaving razor cartridge. Those of skill in the art will understand that shaving aids are also commonly referred to as lubricating strips. Suitable examples of shaving aids and/or lubricating strips are disclosed in U.S. Pat. Nos. 7,069,658; 6,944,952; 6,594,904; 6,182,365; 6,185,822; 6,298,558 and 5,113,585, and U.S. Design Pat. D424,745. In one example, a shaving aid can comprise from about 50% to about 95% of a lubricious water soluble polymer, selected from the group consisting of polyethylene oxide; polyvinyl pyrrolidone, polyacrylamide, modified hydroxyalkyl cellulose, polyvinyl imidazoline, polyvinyl alcohol, polysulfone, polyhydroxyethyl-methacrylate, and mixture thereof. The shaving aid can also include from about 1% to about 50% of a non-soluble polymer selected from the group consisting of polyethylene, polypropylene, polystyrene, butadiene-styrene copolymer, polyacetal, acrylonitrile-butadiene-styrene copolymer, ethylene vinyl acetate copolymer, polyurethante, and mixtures thereof.

Compositions of the present disclosure may include the following components:

A. Detersive Surfactant

Compositions of the present disclosure may include a detersive surfactant. The detersive surfactant component may include an anionic detersive surfactant, a zwitterionic or amphoteric detersive surfactant, or a combination thereof. The concentration of the anionic surfactant component in the composition should be sufficient to provide the desired cleaning and lather performance, and can generally range from about 5% to about 50%.

Anionic surfactants suitable for use in the compositions are the alkyl and alkyl ether sulfates. Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24, or about 10 to about 18, carbon atoms; and M is a cation described hereinbefore. Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinates, examples of which can include disodium N-octadecylsulfosuccinate; disodium lauryl sulfosuccinate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Other suitable anionic detersive surfactants can include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non-limiting example of such an alpha-olefin sulfonate mixture is described in U.S. Pat. No. 3,332,880.

Another class of anionic detersive surfactants suitable for use in the compositions is the beta-alkyloxy alkane sulfonates. These surfactants conform to the formula:

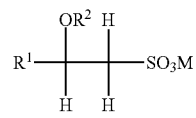

where $R^1$ is a straight chain alkyl group having from about 6 to about 20 carbon atoms, $R^2$ is a lower alkyl group having from about 1 to about 3 carbon atoms, or even 1 carbon atom, and M is a water-soluble cation as described hereinbefore. Further examples of detersive surfactants are described in U.S. Pat. Nos. 3,929,678; 2,658,072; 2,438,091; 2,528,378.

B. Cationic Surfactant System

Composition of the present disclosure may include a cationic surfactant system. The cationic surfactant system can be one cationic surfactant or a mixture of two or more cationic surfactants. If present, the cationic surfactant system can be included in the composition at a level by weight of from about 0.1% to about 10%, from about 0.5% to about 8%, from about 1% to about 5%, or even from about 1.4% to about 4%, in view of balance among ease-to-rinse feel, rheology and wet conditioning benefits.

A variety of cationic surfactants including mono- and di-alkyl chain cationic surfactants can be used in the compositions of the present disclosure. Examples of suitable materials can include mono-alkyl chain cationic surfactants in view of the desired gel matrix and wet conditioning benefits. The mono-alkyl cationic surfactants are those having one long alkyl chain which has from 12 to 22 carbon atoms, from 16 to 22 carbon atoms, or a $C_{18}$-$C_{22}$ alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines Mono-alkyl quaternary ammonium salts include, for example, those having a non-functionalized long alkyl chain. Mono-alkyl amines include, for example, mono-alkyl amidoamines and salts thereof.

Mono-long alkyl quaternized ammonium salts useful herein are those having the formula:

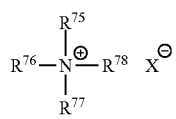

wherein one of $R^{75}$, $R^{76}$, $R^{77}$ and $R^{78}$ are selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. In one aspect, one of $R^{75}$, $R^{76}$, $R^{77}$ and $R^{78}$ is selected from an alkyl group of from 12 to 30 carbon atoms, in another aspect, from 16 to 22 carbon atoms, in another aspect, from 18 to 22 carbon atoms, or even 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Examples of suitable mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Among them, highly useful materials are behenyl trimethyl ammonium salt and stearyl trimethyl ammonium salt.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present disclosure are disclosed in U.S. Pat. No. 4,275,055, Nachtigal, et al. These amines can also be used in combination with acids such as 1-glutamic acid, lactic acid, hydrochloric acid, malic acid, succinic acid, acetic acid, fumaric acid, tartaric acid, citric acid, 1-glutamic hydrochloride, maleic acid, and mixtures thereof; in one aspect, 1-glutamic acid, lactic acid, citric acid are highly useful. In one aspect, amines herein are partially neutralized with any of the acids at a molar ratio of the amine to the acid of from about 1:0.3 to about 1:2, or even from about 1:0.4 to about 1:1.

Although the mono-alkyl chain cationic surfactants are useful, other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

C. High Melting Point Fatty Compound

Compositions of the present disclosure may include a high melting point fatty compound. The high melting point fatty compound useful herein can have a melting point of 25° C. or higher, and can be selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section.

Among a variety of high melting point fatty compounds, fatty alcohols can be used in one aspect the present disclosure. The fatty alcohols useful herein are those having from about 14 to about 30 carbon atoms, or even from about 16 to about 22 carbon atoms. These fatty alcohols are saturated and can be straight or branched chain alcohols. In one aspect, fatty alcohols include, for example, cetyl alcohol, stearyl alcohol, behenyl alcohol, and mixtures thereof.

High melting point fatty compounds of a single compound of high purity are typically used. In one aspect, single compounds of pure fatty alcohols selected from the group of pure cetyl alcohol, stearyl alcohol, and behenyl alcohol are employed. By "pure" herein, what is meant is that the compound has a purity of at least about 90%, or even at least about 95%. These single compounds of high purity provide good rinsability from the hair when the consumer rinses off the composition.

The high melting point fatty compound can be included in the composition at a level of from about 0.1% to about 40%, from about 1% to about 30%, from about 1.5% to about 16% by weight of the composition, or even from about 1.5% to about 8% in view of providing improved conditioning benefits such as slippery feel during the application to wet hair, softness and moisturized feel on dry hair.

D. Cationic Polymers

Compositions of the present disclosure may include a cationic polymer. Concentrations of the cationic polymer in the composition typically range from about 0.05% to about 3%, in another example from about 0.075% to about 2.0%, and in yet another example from about 0.1% to about 1.0%. Suitable cationic polymers can have cationic charge densities of at least about 0.5 meq/gm, in another example at least about 0.9 meq/gm, in another example at least about 1.2 meq/gm, in yet another example at least about 1.5 meq/gm, but in one example also less than about 7 meq/gm, and in another example less than about 5 meq/gm, at the pH of intended use of the composition, which pH will generally range from about pH 3 to about pH 9, in one example between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one example between about 50,000 and about 5 million, and in another example between about 100,000 and about 3 million.

Suitable cationic polymers for use in compositions of the present disclosure can include cationic nitrogen-containing moieties such as quaternary ammonium or cationic protonated amino moieties. The cationic protonated amines can be primary, secondary, or tertiary amines (in one aspect, secondary or tertiary), depending upon the particular species and the selected pH of the composition. Any anionic counterion can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non-limiting examples of such counterions include halides (e.g., chloride, fluoride, bromide, iodide), sulfate and methyl sulfate.

Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, can include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions can include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquatemium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquatemium 6 and Polyquatemium 7, respectively); amphoteric copolymers of acrylic acid including copolymers of acrylic acid and dimethyldiallylammonium chloride (referred to in the industry by CTFA as Polyquatemium 22), terpolymers of acrylic acid with dimethyldiallylammonium chloride and acrylamide (referred to in the industry by CTFA as Polyquatemium 39), and terpolymers of acrylic acid with methacrylamidopropyl trimethylammonium chloride and methyl acrylate (referred to in the industry by CTFA as Polyquatemium 47). In one aspect, cationic substituted monomers may be the cationic substituted dialkylaminoalkyl acrylamides, dialkylaminoalkyl methacrylamides, and combinations thereof. Such monomers conform to the formula:

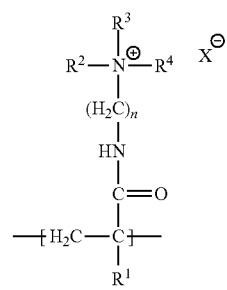

wherein $R^1$ is hydrogen, methyl or ethyl; each of $R^2$, $R^3$ and $R^4$ are independently hydrogen or a short chain alkyl having from about 1 to about 8 carbon atoms, from about 1 to about 5 carbon atoms, or even from about 1 to about 2 carbon atoms; n is an integer having a value of from about 1 to about 8, or even from about 1 to about 4; and X is a counterion. The nitrogen attached to $R^2$, $R^3$ and $R^4$ may be a protonated amine (primary, secondary or tertiary), but is in one aspect, a quaternary ammonium wherein each of $R^2$, $R^3$ and $R^4$ are alkyl groups a non-limiting example of which is polymethacrylamidopropyl trimonium chloride, available under the trade name Polycare® 133, from Rhone-Poulenc, Cranberry, N.J., U.S.A.

Other suitable cationic polymers for use in a composition can include polysaccharide polymers, such as cationic cellulose derivatives and cationic starch derivatives. Suitable cationic polysaccharide polymers include those which conform to the formula:

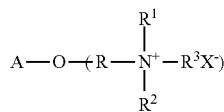

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) is typically about 20 or less; and X is an anionic counterion as described in hereinbefore.

Useful cationic cellulose polymers can include salts of hydroxyethyl cellulose reacted with trimethyl ammonium substituted epoxide, referred to in the industry (CTFA) as Polyquaternium 10 and available from Amerchol Corp. (Edison, N.J., USA) in their Ucare™ Polymer LR, Ucare™ Polymer JR, and Ucare™ Polymer KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the trade name Ucare™ Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance® series commercially available from Aqualon Division of Hercules, Inc. Other suitable cationic polymers include quaternary nitrogen-containing cellulose ethers, some examples of which are described in U.S. Pat. No. 3,962,418. Other suitable polymers include synthetic polymers such as those disclosed in U.S. Publication No. 2007/0207109A1. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

E. Nonionic Polymers

Compositions of the present disclosure may include a nonionic polymer. Polyalkylene glycols having a molecular weight of more than about 1000 are useful herein. Useful are those having the following general formula:

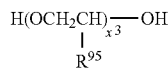

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

F. Conditioning Agents

Conditioning agents, and in particular silicones, may be included in compositions described herein. Conditioning agents include any material which is used to give a particular conditioning benefit to hair and/or skin. In hair treatment compositions, suitable conditioning agents are those which deliver one or more benefits relating to shine, softness, compatibility, antistatic properties, wet-handling, damage, manageability, body, and greasiness. The conditioning agents useful in the compositions of the present disclosure typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

Conditioning agents used in compositions of the present disclosure can be an insoluble silicone conditioning agent. The silicone conditioning agent particles may include volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, from about 0.1% to about 8%, from about 0.1% to about 5%, or even from about 0.2% to about 3%. Non-limiting examples of suitable silicone conditioning agents, and optional suspending agents for the silicone, are described in U.S. Reissue Pat. No. 34,584; U.S. Pat. No. 5,104,646 and U.S. Pat. No. 5,106,609. The silicone conditioning agents for use in compositions of the present disclosure typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 cst.

The dispersed silicone conditioning agent particles can typically have a number average particle diameter ranging from about 0.01 μm to about 50 μm. For small particle application to hair, the number average particle diameters typically range from about 0.01 μm to about 4 μm, from about 0.01 μm to about 2 μm, or even from about 0.01 μm to about 0.5 μm. For larger particle application to hair, the number average particle diameters typically range from about 4 μm to about 50 μm, from about 6 μm to about 30 μm, from about 9 μm to about 20 μm, or even from about 12 μm to about 18 μm.

a. Silicone Oils

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in compositions of the present disclosure can include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

b. Amino and Cationic Silicones

Compositions of the present disclosure may include an aminosilicone. Aminosilicones, as provided herein, are silicones containing at least one primary amine, secondary amine, tertiary amine, or a quaternary ammonium group. Useful aminosilicones may have less than about 0.5% nitrogen by weight of the aminosilicone, less than about 0.2%, or even less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present disclosure.

In one aspect, the aminosilicones used in the present disclosure can have a particle size of less than about 50μ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one example, the aminosilicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This example may also include a low viscosity fluid, such as, for example, those materials described herein. The viscosity of aminosilicones discussed herein is measured at 25° C.

In another example, the aminosilicone typically has a viscosity of from about 1,000 cst to about 100,000 cst, from about 2,000 cst to about 50,000 cst, from about 4,000 cst to about 40,000 cst, or even from about 6,000 cst to about 30,000 cs.

The aminosilicone typically is contained in the composition of the present disclosure at a level by weight of from about 0.05% to about 20%, from about 0.1% to about 10%, and or even from about 0.3% to about 5%.

c. Silicone Gums

Other silicone fluids suitable for use in compositions of the present disclosure are the insoluble silicone gums. These gums are polyorganosiloxane materials having a viscosity, as measured at 25° C., of greater than or equal to 1,000,000 csk. Specific non-limiting examples of silicone gums for use in the compositions of the present disclosure include poly- dimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in compositions of the present disclosure are those known as "high refractive index silicones," having a refractive index of at least about 1.46, at least about 1.48, m at least about 1.52, or even at least about 1.55. The refractive index of the polysiloxane fluid will generally be less than about 1.70, typically less than about 1.60. In this context, polysiloxane "fluid" includes oils as well as gums.

A high refractive index polysiloxane fluid includes those represented by the general formula:

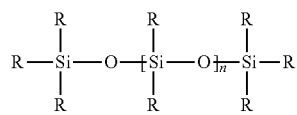

wherein each R independently can be a substituted or an unsubstituted aliphatic (e.g. alkyl or alkenyl), aryl, aryloxy, alkaryl, alkoxy, alkamino (e.g. alkyl or alkenyl amino groups), hydroxy, or hydrogen, or combinations thereof; and n is an integer of about 1 or more, and from about 1 to about 1,000. The R substituents can also include combinations of ether groups, hydroxy groups, and amine groups, as well as other functional groups, such as halogens and halogen-substituted functionalities, e.g. halogen-substituted aliphatic and aryl groups. High refractive index polysiloxiane fluids also include cyclic polysiloxanes such as those represented by the formula below:

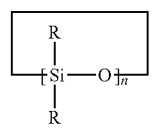

wherein R is as defined above, and n is a number from about 3 to about 7, or even from about 3 to about 5.

Silicone fluids suitable for use in the compositions of the present disclosure are disclosed in U.S. Pat. No. 2,826,551; U.S. Pat. No. 3,964,500 and U.S. Pat. No. 4,364,837.

e. Silicone Resins

Silicone resins may be included in the conditioning agent of compositions of the present disclosure. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence.

In one example, silicone resins for use in compositions of the present disclosure can include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from about 0.5:1.0 to about 1.5:1.0 and the average molecular weight of the silicone resin is typically from about 1000 to about 10,000.

f. Modified Silicones or Silicone Copolymers

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in U.S. Patent Application Publication Nos. 2007/0286837A1 and 2005/0048549A1.

In addition, the above-noted silicone-based quaternary ammonium compounds may be combined with the silicone polymers described in U.S. Pat. Nos. 7,041,767 and 7,217,777 and U.S. Patent Application Publication No. 2007/0041929A1.

2. Organic Conditioning Oils

Compositions of the present disclosure may also include from about 0.05% to about 3%, from about 0.08% to about 1.5%, or even from about 0.1% to about 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about $C_{12}$ to about $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to about $C_{14}$ or even $C_6$ to about $C_{12}$. Suitable fatty esters include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Other Conditioning Agents

Also suitable for use in compositions herein are the conditioning agents described by the Procter & Gamble Company in U.S. Pat. Nos. 5,674,478 and 5,750,122. Also suitable for use herein are those conditioning agents described in U.S. Pat. Nos. 4,529,586; 4,507,280; 4,663,158; 4,197,865; 4,217, 914; 4,381,919 and 4,422, 853.

4. Anti-Dandruff Actives

Compositions of the present disclosure may also contain an anti-dandruff agent.

Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753 and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

5. Humectant

Compositions of the present disclosure may include a humectant. The humectants herein are selected from the group consisting of polyhydric alcohols, water soluble alkoxylated nonionic polymers, and mixtures thereof. The humectants, when used herein, are typically used at levels of from about 0.1% to about 20%, or even from about 0.5% to about 5%.

6. Suspending Agent

Compositions of the present disclosure may further include a suspending agent at concentrations effective for suspending water-insoluble material in dispersed form in the compositions or for modifying the viscosity of the composition. Such concentrations range from about 0.1% to about 10%, or even from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein can include Carbomers with trade names Carbopol® 934, Carbopol® 940, Carbopol® 950, Carbopol® 980, and Carbopol® 981, all available from B. F. Goodrich Company, acrylates/steareth-20 methacrylate copolymer with trade name ACRYSOL™ 22 available from Rohm and Hass, nonoxynyl hydroxyethylcellulose with trade name Amercell™ POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one example having from about 16 to about 22 carbon atoms. In one example, useful suspending agents include ethylene glycol stearates, both mono and distearate, but in one example, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine Still other suitable suspending agents include di(hydrogenated tallow)phthalic acid amide, and crosslinked maleic anhydride-methyl vinyl ether copolymer.

7. Aqueous Carrier

Compositions of the present disclosure can be in the form of pourable liquids (under conditions). Such compositions will therefore typically include an aqueous carrier, which is present at a level of from about 20% to about 95%, or even from about 60% to about 85%. The aqueous carrier may include water, or a miscible mixture of water and organic solvent, and in one example may include water with minimal or no significant concentrations of organic solvent, except as otherwise incidentally incorporated into the composition as minor ingredients of other essential or optional components.

The carrier useful in the present disclosure includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

8. Gel Matrix

The above cationic surfactants, together with high melting point fatty compounds and an aqueous carrier, may form a gel matrix in the composition of the present disclosure.

A gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, or even from about 1:1 to about 1:6.

Method of Making Shampoo Formulations

Any suitable method of making a shampoo may be used. In one example, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

Method of Making Conditioner Formulations

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone is added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stirring to assure homogenization. After it is homogenized, it is cooled to room temperature. A triblender and/or mill can be used in each step, if necessary to disperse the materials.

Compact Formulations

The present disclosure can also be used in a compact hair care formulation. A compact formula is a formula which delivers the same benefit to the consumer at a lower usage level. Compact formulations and methods of making compact formulations are described in U.S. Application Publication No. 2009/0221463A1.

Processes of Making

Compositions of the present disclosure can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

In one example, a process of making a composition comprising combining an adjunct ingredient and, based on total composition weight, and from about 0.1% to about 50%, from about 0.2% to about 25%, from about 0.5% to about 10%, or even from about 0.75% to about 5% microcapsules, each of said microcapsules independently having a particle size of from about 2 microns to about 80 microns, from about 5 microns to about 50 microns or even from about 10 microns to about 30 microns, each microcapsule as disclosed herein. Said microcapsules may be contained in a slurry or dried and combined with an adjunct ingredient.

Experimental

Test Methods
Hair Switch Treatment Method

In a Hair Switch Treatment method, moderately damaged general population hair from International Hair Importers was obtained and made into hair switches of the following size: 4 grams and 8 inches. The hair switches are then stored with foil, tissue paper, or a kim wipe. Paper towels can contain silicone and are therefore, not used to avoid any additional contamination to the hair.

Test Set-Up: Preparation/Labeling
Hair Switches

Depending on the number of switches per product that is requested (standard is 2), hair switches should be labeled to correspond with the product sample codes. Marked switches are then hung on a cart in corresponding order.

Switch Treatment Conditions:
1. Constant Water Temperature

A temperature gauge should be installed at the sink to ensure a constant temperature throughout the treatment portion of the test. The standard temperature should be set at 100 degrees F.+/−3 degrees F.

2. Constant Water Pressure

The pressure of the rinse water must be regulated for rinsing consistency. A flow meter should be installed at the sink and adjusted to standard measurement of 1.5 gallons per minute+/−0.25 gpm.

3. Water Hardness—an average of 7-13 grain.

4. Milking and Rinsing Guidelines—milk at a rate of 50-60 strokes per 30 seconds. The milking procedure (stroking motion from top to bottom) is very critical to achieving consistent results from each switch within the confines of a product. A consistent milking pattern, maintaining that pattern and a constant rhythm throughout the treatment of all switches is critical. Milk the switch hard enough to allow the product to come in contact with the hair through its thickness and not just the outer layers.

5. A stationary shower rinse is used with no additional manipulation of the hair for 30 seconds. Lightly squeegee once down the switch from top to bottom between fingers after rinsing to remove excess water.

Treatment Procedure—1 Cycle

1) Requirement: wear vinyl gloves during the treatment process changing between every switch.
2) Use a separate 1 cc disposable syringe for each product application.
3) Standard product amount: 0.1 cc (equivalent to approximately 0.1 grams) per gram of hair.
4) Avoid contamination: handle switches by taped top and avoid contact with other switches/surfaces.
5) Pull up required product amount into syringes for each test product (make sure no air bubbles are in the syringe).
6) When the product is a cream, apply conditioner product (0.10 cc per gram of hair) evenly from top to bottom starting 1 inch down from the clamp using a 1 ml disposable syringe.
    a. Milk 50-60 strokes/30 seconds.
    b. Then hang on drying cart at ambient temperature and approximately 30% relative humidity.
7) When the product is a spray, prepare the hair switch in the following manner:
    a. Zero a large weigh boat with a 10 gram, 10 inch hair switch on the scale.
    b. Bring hair switch to sink, spray to cover length of switch. Spray should be roughly 6 inches from the switch while spraying.
    c. Start with 2 sprays front and back (total of 4), covering evenly top to bottom on each side.
    d. Weigh, and add more sprays as needed.
    e. Weigh: confirm that ~1 gram of product has been applied to hair (±10%).
    f. If under, apply additional product 1 spray at a time and measure (alternating sides of the switch for each additional spray).
    g. If over, get new switch.
    h. Comb to detangle—~3 combs on front, starting from bottom and working up (or as many combs as needed to untangle the hair).
    i. Then hang on drying cart at ambient temperature and approximately 30% relative humidity.

Olfactive Analysis Method

Once switches have been treated according to the Hair Switch Treatment method, the switches should be allowed to dry for at least 4 hours at 70° F./30% RH:

1) A perfumer or trained panelist assesses the fragrance on the hair switch by bringing the middle portion of the hair switch to the nose, and making an olfactive assessment. The Primavera olfactive grade is recorded as "initial pre-comb".
2) Next, a perfumer or trained panelist combs the hair switch 3× with the fine tooth side of a comb (11 cm long—teeth to teeth, 1.5 cm long teeth, teeth spaced approximately 0.10 cm apart), and then brings the middle portion of the hair switch to the nose, and makes an olfactive assessment. The Primavera olfactive grade is recorded as "initial post-comb".
3) In this manner, multiple combing sequences can be completed at different time points, using the same hair switch, in order to collect perfume intensity data.
4) The olfactive intensity scale ratings are given below.

| Olfactive Grade | Concentration of DihydroMyrcenol in mineral oil | Descriptors |
| --- | --- | --- |
| 0 | 0% | No Odor |
| 25 | 0.005% | Weak |
| 50 | 0.2% | Moderate |
| 75 | 2% | Strong |
| 100 | 100% | Very Strong |

A difference of 5 points on this scale is not considered a noticeable difference on hair. A 10 point difference in olfactive grade is large and noticeable.

Examples/Combinations

A. A microcapsule comprising: a core material miscible with a lipophilic phosphate ester; and a shell wall at least partially surrounding the core material, the shell wall comprising the reaction product of the lipophilic phosphate ester and a multivalent ion.
B. The microcapsule of paragraph A, wherein the core material has a C log P value of 0 or greater, 1 to 5, or 3 to 4.5.
C. The microcapsule of paragraphs A or B, wherein the core material comprises perfume oil.
D. The microcapsule of paragraphs A-C, wherein the core material is polar.
E. The microcapsule of paragraphs A-D, wherein the microcapsule is encapsulated in a starch matrix.
F. The microcapsule of paragraph E, wherein the starch matrix comprises an octenylsuccinic acid anhydride modified starch.
G. The microcapsule of paragraphs A-F, wherein the lipophilic phosphate ester comprises a phosphate alcohol ester.
H. The microcapsule of paragraphs A-G, wherein the lipophilic phosphate ester comprises a phosphate diester.
I. The microcapsule of paragraphs A-H, wherein the lipophilic phosphate ester has an acid value of about 950 mg KOH/g or less phosphate ester.
J. The microcapsule of paragraphs A-JI, wherein the lipophilic phosphate ester has an acid value of 180 mg KOH/g phosphate ester to 450 mg KOH/g phosphate ester.
K. The microcapsule of paragraphs A-J, wherein the lipophilic phosphate ester comprises an R-group having a carbon chain length of 6 to 18 carbons.
L. The microcapsule of paragraph K, wherein the R-group is a $C_8$ to $C_{10}$ linear alkyl chain.
M. The microcapsule of paragraphs A-L, wherein the multivalent ion comprises one or more of aluminum sulfate, chitosan, polyethyleneimine, and polydiallyldimethylammonium chloride.
N. The microcapsule of paragraphs A-M, wherein the microcapsule has a diameter from 10 microns to 30 microns.
O. The microcapsule of paragraphs A-N, wherein the shell wall has an average thickness of 1 micron.
P. The microcapsule of paragraphs A-O, wherein the microcapsule is rupturable with one or more of time, humidity, and friction.
Q. The microcapsule of paragraphs A-P is a benefit delivery agent.
R. A personal care composition comprising a one or more of the microcapsules of paragraphs A-Q.
S. A microcapsule comprising: a core material at least partially encapsulated by a phosphate ester salt; wherein the core material has a C log P value of 0 or greater, 1 to 5, or 3 to 4.5; and the phosphate ester salt comprises an R-group having a carbon chain length of 6 to 18 carbon atoms.
T. The microcapsule of paragraph S, wherein the phosphate ester salt comprises the salt of a phosphate ester and a multivalent ion.
U. The microcapsule of paragraphs R-T, wherein the multivalent ion comprises one or more of aluminum sulfate, chitosan, polyethyleneimine, and polydiallyldimethylammonium chloride.
V. A composition comprising: an adjunct ingredient; and one or more microcapsules, wherein each of the one or more microcapsules comprises: a core material miscible with a lipophilic phosphate ester; and a shell wall comprising the reaction product of the lipophilic phosphate ester and a multivalent ion.
W. The composition of paragraph V, wherein the core material has a C log P value of 0 or greater, 1 to 5, or 3 to 4.5.
X. The composition of paragraphs V-W, wherein the one or more microcapsules are benefit delivery agents.
Y. The composition of paragraphs V-X, wherein the core material comprises a perfume oil.
Z. The composition of paragraphs V-Y, wherein the composition exhibits a longer fragrance duration than an alternative composition free of the one or more microcapsules.
AA. The composition of paragraphs V-Z, wherein the composition is a personal care composition comprising one of a shampoo, conditioner, deodorant, or antiperspirant.
BB. The composition of paragraphs V-AA, wherein the one or more microcapsules are rupturable with one or more of time, humidity, and friction.
CC. The composition of paragraphs V-BB, wherein the adjunct ingredient comprises one or more of cationic polymers, surfactants, builders, chelating agents, dye transfer inhibiting agents, dispersants, enzymes, enzyme stabilizers, catalytic materials, bleach activators, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids and pigments.

EXAMPLES

Example 1

To study the suitability of various phosphate esters, various compositions Samples A to I were produced, each containing a perfume oil and a different phosphate ester in a 9:1 perfume to phosphate ester ratio. As depicted in Table 2, each Sample was added to deionized water, 10% weight aluminum sulfate, and 10% weight polyDADMAC to evaluate the formation of an oil/water interface, as well as the formation of any precipitates. The phosphate esters were commercially obtained from Lakeland Labs Ltd.

TABLE 2

| Sample | Phosphate Ester (Lakeland Labs Ltd.) | Monoester/Diester | Acid Value (mg KOH/g phosphate ester) |
| --- | --- | --- | --- |
| A | PPE-1614 Phosphate Phenol Ethoxylate Ester | Mono and Di | 180 |

TABLE 2-continued

| Sample | | | | |
|---|---|---|---|---|
| B | PAE-803 Phosphate Alcohol Ethoxylate Ester | Mono and Di | | 190 |
| C | PAE-136 Phosphate Alcohol Ethoxylate Ester | Mono and Di | | 200 |
| D | PAE-147 Phosphate Alcohol Ethoxylate Ester | Mono | | 220 |
| E | PA-900 Phosphate Alcohol Ester | Mono and Di | | 275 |
| F | PA-604 Phosphate Phenol Ethoxylate Ester | Mono | | 320 |
| G | PA-800 Phosphate Alcohol Ester | Mono and Di | | 360 |
| H | PA-400 Phosphate Alcohol Ester | Mono and Di | | 460 |
| I | PA-100 Phosphate Alcohol Ester | Mono | | 950 |

| Sample | Perfume/Phosphate Ester 90/10 Behavior in Water | Perfume/Phosphate Ester 90/10 Behavior in 10 wt % Aluminum Sulfate | Perfume/Phosphate Ester 90/10 Behavior in 10 wt % polyDADMAC | Result |
|---|---|---|---|---|
| A | Part of oil sinks to bottom; after agitation, all oil floats to top | Precipitate observed | Oil droplets surrounded by a white colored precipitate; droplets appear to be stabilized | Dissolves into aqueous phase (emulsifier) |
| B | Precipitate and stable emulsion | Precipitate observed, stable milky white emulsion | White precipitate observed | Dissolves into aqueous phase (emulsifier) |
| C | Precipitate and stable emulsion | Precipitate observed | White precipitate observed | Dissolves into aqueous phase (emulsifier) |
| D | Precipitate and stable emulsion | Precipitate observed, stable milky white emulsion | White precipitate observed | Dissolves into aqueous phase (emulsifier) |
| E | No precipitate, individual oil particles don't coalesce | Precipitate observed; oil phase viscosity increased; irregularly shaped oil droplet floating on top of water | Viscous paste | Soluble in perfume oil, precipitate at interface, does not dissolve into aqueous phase |
| F | Precipitate and stable emulsion | Immediate precipitate observed | Droplets appear to be stabilized | Dissolves into aqueous phase (emulsifier) |
| G | No precipitate, one coalesced oil droplet on top of water | No precipitate observed | Droplets appear to be stabilized | Soluble in perfume oil; no precipitate at oil-water interface |
| H | Oil sinks to bottom; after agitation, floats to top | Precipitate observed | Droplets appear to be stabilized | Dissolves into aqueous phase (emulsifier) |
| I | 90% of oil sinks to bottom and becomes a ball surrounded by white precipitate. After agitation, oil remains on bottom and coalesces into one drop | White precipitate observed surrounding droplet of oil | White precipitate observed | Reacts with perfume oil to form a dark brown solution, precipitation observed |

As depicted by Table 2, Sample E formed of a phosphate alcohol ester exhibited the best results. Specifically, Sample E was miscible with a perfume oil, did not dissolve into the aqueous phase, and formed precipitates with both the aluminum sulfate solution and the polyDADMAC solution at the oil-water interface.

Example 2

Example 2 is a Comparative Example of a microcapsule formed without a phosphate ester. Example 2 is formed through the preparation of several solutions:

Solution A includes 72 grams of perfume oil, 8 grams of brominated vegetable oil (Spectrum V1032) and is prepared with gentle agitation. Solution A is transparent and homogeneous.

Solution B includes approximately 9 grams of chitosan (TCI C2395), 291 grams of water at 80° C., and 2.0 grams of glacial acetic acid (Amresco). Solution B was prepared by adding the chitosan to the water and agitating the solution using a 3-blade pitched turbine agitator. The powder was added into the vortex and allowed to wet. Next, the glacial acetic acid was added to reduce the pH to 3.5. The contents were left to agitate at 80° C. for 10 minutes, then allowed to cool. The dissolved chitosan solution was left to sit overnight before use.

Solution C includes 76 grams of HICAP 100 (Ingredion), and 227 grams of deionized water at 70° C. The solution was agitating with a 3-blade pitched turbine agitator at 740 RPM. The HICAP 100 was added into the vortex and allowed to wet prior to adding additional HICAP 100. The mixture was allowed to agitate for 30 minutes, and then allowed to defoam overnight at room temperature with no agitation. The pH of the solution at room temperature is 4.15

Example 2 was formed by adding approximately 7.31 grams of Solution A to 79.8 grams of Solution C, while agitating at 500 RPM using a IKA Laboretechnik mixer (3-blade turbine agitator blade) over a duration of 30 seconds. The solution was then allowed to mix for 1 minute. Next, 66.5 grams of Solution B was added slowly to the mixture. Finally, approximately 7.47 grams of 10 weight percent aluminum sulfate solution was added to the suspension.

Example 3

Example 3 is a Comparative Example of a spray dried microcapsule formed without a phosphate ester. Example 3 is formed through the preparation of several solutions:

Solution A was prepared by mixing 40.12 grams of aluminum sulfate (Sigma Lot SLBF0512V) to deionized water (Omnipur 98072052) to obtain a homogeneous, transparent solution.

Solution B was prepared by mixing 124.5 grams of octenyl succinic acid anhydride modified starch (HICAP 100, Ingredion Lot DCI6638) into 370.5 grams of water at preheated to 70 degrees Celsius. Next, 6.5 grams of 4, 5-imidazolidine-3-one (Sigma) was added, followed by 2.61 grams of ammonium chloride (Sigma).

Solution C was prepared by slowly adding 52 grams of perfume oil to 462.5 grams of Solution B at a temperature of 25° C., and then homogenizing said mixture for 3 minutes at 24,000 RPM using an Ultra Turrax T25 mixer. 47 grams of Solution A was then added with mixing.

The resultant Solution D was then pumped into a Niro spray dryer, 3 ft diameter, centrifugal wheel atomizer, with co-current airflow that has an inlet air temperature of 200° C. The flow of Solution D into the spray dryer was manipulated to achieve an outlet air temperature between 95° C. and 105° C. The approximate dry basis composition of the spray dried particle is depicted in Table 3 below.

TABLE 3

| Material | Weight Percentage |
| --- | --- |
| HICAP 100 Starch | 67.1% |
| Al2(SO4)3 | 2.7% |
| Perfume | 30.2% |
| Phosphate Ester | 0% |
| % Yield from Dryer | 85% |

Example 4

Example 4 is an Inventive Example formed with a shell wall incorporating a phosphate ester. Example 4 was formed from the following solutions:

Solution A was prepared by mixing 40.12 grams of aluminum sulfate (Sigma Lot SLBF0512V) with deionized water (Omnipur 98072052) to obtain a homogeneous, transparent solution.

Solution B was prepared by mixing 50.02 grams of phosphate ester PA-900 (Lakeland Laboratories Ltd) in 202.4 grams of perfume oil.

Solution C was prepared by mixing 124.5 grams of octenyl succinic acid anhydride modified starch (HICAP 100, Ingredion Lot DCI6638) into 370.5 grams of water preheated to 70° C. Next, 6.5 grams of 4, 5-imidazolidine-3-one (Sigma) was added, followed by 2.61 grams of ammonium chloride (Sigma).

Solution D was prepared by slowly adding 72.5 grams of Solution B to 462.5 grams of Solution C at a temperature of 25° C., and homogenizing for 3 minutes at 24,000 RPM using an Ultra Turrax T25 mixer. Subsequently, 52 grams of Solution A was then added with mixing. Solution D was then pumped into a Niro spray dryer, 3 ft diameter, centrifugal wheel atomizer, with co-current airflow that has an inlet air temperature of 200° C. The flow of Solution D into the spray dryer was manipulated to achieve an outlet air temperature between 95° C. and 105° C. The approximate dry basis composition of the spray dried particle is depicted in Table 4 below.

TABLE 4

| Material | Weight Percentage |
| --- | --- |
| HICAP 100 Starch | 59.4% |
| Al2(SO4)3 | 2.7% |
| Perfume | 30.3% |
| Phosphate Ester | 7.6% |
| % Yield from Dryer | 87% |

Figure 2:
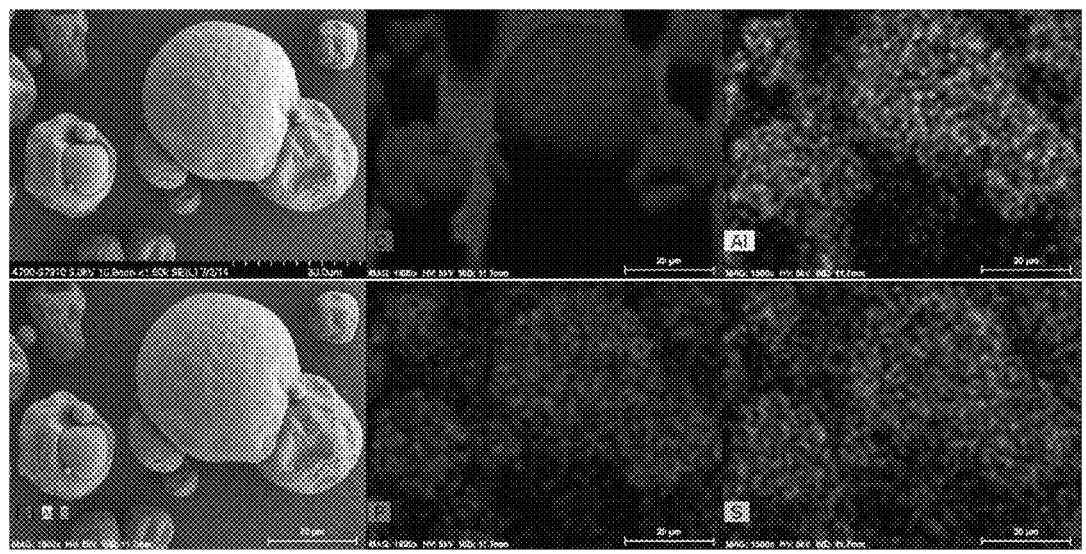
FIG. 2 depicts cryo-SEM scans illustrating the elemental composition of inventive microcapsules.

Example 4 was analyzed by Cryo-SEM to better understand particle morphology and understand elemental distribution across the surface of the microcapsules. Two types of particles were observed: smooth surface particles that are highly spherical and particles with a wrinkled surface with dents. Both particles exhibited similar elemental compositions. Aluminum and phosphate were found on every capsule (the elemental analysis penetration depth was about 1 micron, and the particle size is on the order of 20 microns). Very few broken particles were observed. Cryo-SEM scans are reproduced in FIGS. 1 and 2.

Table 5 depicts the encapsulation efficiency of Comparative Example 3 and Inventive Example 4. Samples of each example were prepared by dispersing approximately 0.33 g of each Example in 10 mL of deionized water in a 50 mL centrifuge tube. The samples were vortexed for 20 seconds, roll mixed for 10 minutes, and then vortexed for another 20 seconds. The remaining percentage of encapsulated perfume oil encapsulated was then evaluated by adding 20 mL of hexane or 20 mL of ethanol and centrifuging at 500 RPM for 1 minute to isolate the organic layer. The hexane or ethanol was then evaluated with gas chromatography and mass spectroscopy to determine the percentage of perfume oil extracted. For extraction with ethanol, each sample was heated to 60° C. for 30 minutes after addition of ethanol but before centrifuging.

TABLE 5

| Sample Description | % hexane extractable perfume oil | % ethanol extractable perfume oil |
|---|---|---|
| Perfume Oil Control | 100% | 100% |
| Example 3 - Starch Encapsulated Perfume Oil without Phosphate Ester PA-900 | 100% | 100% |
| Example 4 - Starch Encapsulated Perfume Oil with Phosphate Ester PA-900 | 23% | 82% |

As depicted by Table 5, the microcapsules of Inventive Example 4 retained significantly higher quantities of the perfume oil than microcapsules of Comparative Example 3 which did not include a phosphate ester.

Example 5

Example 5 evaluates the use of different core materials by determining their miscibility with a suitable phosphate ester (PA-900 from Lakeland Laboratories Ltd.). Samples A to L were formed of two samples each of: glycerin; polyethylene glycol 400 ("PEG 400"); Dow Corning 200 Fluid (polydimethylsiloxane; obtained from Dow Corning); menthol/menthyl lactate 50/50 mixture; isopropyl myristate (obtained from IFF); and permethyl 101a (obtained from Preperse Corp.).

TABLE 6

| Sample | Glycerin (g) | PEG 400 (g) | Dow 200 Fluid (g) | Menthol/ Menthyl Lactate (g) | IPM (g) | Permethyl 101a (g) | PA-900 (g) | Comments |
|---|---|---|---|---|---|---|---|---|
| A | 9.127 | | | | | | 1.060 | Cloudy dispersion; 1 single phase |
| B | 9.467 | | | | | | 0.603 | Cloudy dispersion; 1 single phase |
| C | | 9.014 | | | | | 1.067 | transparent soln, clear white, 1 phase; agitation introduces haze |
| D | | 9.704 | | | | | 0.484 | transparent soln, clear white, 1 phase; agitation introduces haze |
| E | | | 9.189 | | | | 1.038 | fully miscible, 1 phase, transparent, homogeneous, clear white |
| F | | | 9.866 | | | | 0.524 | fully miscible, 1 phase, transparent, homogeneous, clear white |
| G | | | | 9.025 | | | 1.030 | fully miscible, 1 phase, transparent, homogeneous, clear white |
| H | | | | 9.528 | | | 0.645 | fully miscible, 1 phase, transparent, homogeneous, clear white |
| I | | | | | 9.001 | | 1.024 | fully miscible, 1 phase, transparent, homogeneous, clear white |
| J | | | | | 9.545 | | 0.701 | fully miscible, 1 phase, transparent, homogeneous, clear white |
| K | | | | | | 9.036 | 1.122 | fully miscible, 1 phase, transparent, homogeneous, clear white |

TABLE 6-continued

| Sample | Glycerin (g) | PEG 400 (g) | Dow 200 Fluid (g) | Menthol/ Menthyl Lactate (g) | IPM (g) | Permethyl 101a (g) | PA- 900 (g) | Comments |
|---|---|---|---|---|---|---|---|---|
| L | | | | | | 9.518 | 0.574 | fully miscible, 1 phase, transparent, homogeneous, clear white |

As depicted by Table 6, the miscibility of the core materials is not determined by polarity. For example, menthol/menthyl lactate was fully miscible in the phosphate ester despite being a polar compound.

Example 6

Microcapsules having various core materials were formed. Sample 1 includes a perfume oil core, Sample 2 includes a Dow Corning 200 silicone fluid core, Sample 3 includes a 50/50 blend of menthol and menthyl lactate core. Each sample was formed by mixing the lipophilic core with a Polyethylenimine aqueous solution. The Polyethylenimine aqueous solution was formed of 70.0 grams Luprasol WF (obtained from BASF Chemical Co.) and 630.3 g deionized water. Microcapsules of each sample were formed by mixing the following solutions with the Polyethylenimine aqueous solution depicted in Table 7.

The lipophilic core of Sample 1 included 3.21 g of phosphate ester PA-900 (obtained from Lakeland Laboratories Ltd.) and 12.82 g of perfume oil.

The lipophilic core of Sample 2 was formed of 3.4 g of phosphate ester PA-900 (obtained from Lakeland Laboratories Ltd.) and 12.80 of Dow Corning 200 silicone fluid.

The lipophilic core of Sample 3 was formed of 3.48 g of phosphate ester PA-900 (obtained from Lakeland Laboratories Ltd.) and 3.48 g of a 50/50 blend of menthol and menthyl lactate.

TABLE 7

| Sample | Core Material Description | Actual Core Material (g) | Solution Z (g) | Microscopy |
|---|---|---|---|---|
| 1 | Perfume Oil | 5.052 | 100.053 | Capsules observed |
| 2 | Silicone 200 Fluid | 5.072 | 100.041 | Capsules observed |
| 3 | Menthol/ Menthyl Lactate | 4.933 | 100.019 | Capsules observed |

As depicted by Table 7, each of the core materials was successfully encapsulated by the phosphate ester microencapsulation process.

Examples 7 to 13

Examples of various leave-on conditioner products were produced including Perfume Microcapsule Samples 1 to 3. Perfume Microcapsule Samples 1 to 3 were produced using the following solutions:

Solution A was prepared by adding 250 grams of HICAP 100 (obtained from Ingredion) to 750 g of deionized water preheated to 70° C. Mixing was continued until a homogeneous solution of starch was obtained.

Solution B was prepared by adding 27.4 g of chitosan (obtained as TCI C2395 from TCI America) with 874.4 g of deionized water heated to 90° C. After dispersing the powder, glacial acetic acid (obtained from Amresco) was used to adjust the pH of the solution to 3.5. The chitosan solution was allowed to cool overnight.

Solution C was prepared by adding 15.85 g of polydiallyl dimethyl ammonium chloride (obtained as Mirapol 100 from Solvay Chemicals) to 34.42 g water.

Solution D was prepared by adding 5.06 g Polyethylenimine (obtained as Lupasol WF from BASF Chemical) to 444.85 g deionized water.

Solution E was prepared by mixing 14.0 g brominated vegetable oil, 75 g perfume oil, and 13.6 g phosphate ester PA-900 (obtained from Lakeland Chemical Ltd.) to form a homogeneous solution.

Microcapsules were prepared by mixing Solution E with Solution A to form an oil-in-water emulsion and then reacting the resulting emulsion with one of Solutions B, C, or D to form Microcapsule Samples 1 to 3. The quantities of each mixing step are depicted in Table 8. Microcapsule Sample 1 is a chitosan/phosphate ester microcapsule; Microcapsule Sample 2 is a polyDADMAC/phosphate ester microcapsule; and Microcapsule Sample 3 is a Polyethylenimine/phosphate ester microcapsule.

TABLE 8

| Microcapsule Sample | Solution A (g) | Interfacial Reaction Medium Solution ID | Solution E (g) | Interfacial Reaction Medium Solution (g) |
|---|---|---|---|---|
| 1 | 80.52 | B | 7.324 | 66.62 |
| 2 | 80.01 | C | 7.275 | 19.87 |
| 3 | 79.18 | D | 7.338 | 19.89 |

Microcapsule Samples 1 to 3 were formulated into a leave-on conditioner matrix configured to deliver 0.40 weight percent perfume (equivalent to delivering 400 micrograms of perfume oil per gram of hair using the Olfactive Analysis of Leave-On Treatment Product Test Method).

TABLE 9

| Material | Example 7 (grams) | Example 8 (grams) | Example 9 (grams) | Example 10 (grams) | Example 11 (grams) | Example 12 (grams) | Example 13 (grams) |
|---|---|---|---|---|---|---|---|
| PREMIX | | | | | | | |
| Water | 22.89 | 22.89 | 22.89 | 22.89 | 22.89 | 22.89 | 22.89 |
| Silicone | 0.57 | 0.57 | 0.57 | 0.57 | 0.47 | 0.57 | 0.67 |
| Cetyl, Stearyl, Oleyl alcohol | 0.59 | 0.59 | 0.59 | 0.59 | 0.49 | 0.49 | 0.49 |
| Behenyl Trimethylammonium chloride BTMAC | 0.21 | 0.21 | 0.21 | 0.21 | 0.11 | 0.11 | 0.21 |
| Stearamidopropyl Dimethylamine | 0.35 | 0.35 | 0.35 | 0.35 | 0.45 | 0.45 | 0.45 |
| Preservatives | 0.50 | 0.50 | 0.50 | 0.50 | 0.50 | 0.40 | 0.50 |
| EDTA | 0.22 | 0.22 | 0.22 | 0.22 | 0.22 | 0.32 | 0.22 |
| Panthenyl ethyl ether | 0.31 | 0.31 | 0.31 | 0.31 | 0.41 | 0.31 | 0.31 |
| Hydroxyethyl cellulose | 0.32 | 0.32 | 0.32 | 0.32 | 0.42 | 0.42 | 0.32 |
| Polyethylene glycol PEG 2M | 0.28 | 0.28 | 0.28 | 0.28 | 0.38 | 0.28 | 0.28 |
| Quaternium-18 | 0.32 | 0.32 | 0.32 | 0.32 | 0.32 | 0.32 | 0.32 |
| Citric acid - anhydrous | 0.22 | 0.22 | 0.22 | 0.22 | 0.22 | 0.22 | 0.22 |
| POST-ADDS | | | | | | | |
| Perfume Oil | 0.107 | 0.00 | 0.00 | 0.00 | 0.00 | 0.00 | 0.00 |
| Microcapsule Sample 1 | 0.00 | 2.89 | 0.00 | 0.00 | 2.89 | 0.00 | 0.00 |
| Microcapsule Sample 2 | 0.00 | 0.00 | 1.96 | 0.00 | 0.00 | 1.96 | 0.00 |
| Microcapsule Sample 3 | 0.00 | 0.00 | 0.00 | 1.99 | 0.00 | 0.00 | 1.99 |
| Water | 2.80 | 0.00 | 0.92 | 0.90 | 0.00 | 0.92 | 0.90 |
| % Perfume in Product | 0.42% | 0.40% | 0.40% | 0.40% | 0.40% | 0.40% | 0.40% |

The Hair Switch Treatment method was used to prepare hair switches using the above leave-on conditioners. The Olfactive Analysis Method was then used to evaluate the perfume bloom delivered from hair switches. As depicted by Table 10, Microcapsule Samples 1 to 3 deliver a noticeable increase fragrance intensity on hair after aging the products for 1 week at 40° C.

TABLE 10

| Leave-on Conditioner Example | Description | 4 hr Olfactive (Pre-/Post-Comb) |
|---|---|---|
| 7 | Perfume Oil | 35+/35 |
| 8 | Chitosan/Phosphate Ester Microcapsules | 40/60 |
| 9 | PolyDADMAC/Phosphate Ester Microcapsules | 35+/50 |
| 10 | Polyethylenimine/Phosphate Ester Microcapsules | 35/45 |

Example 14

Microcapsule Samples 1 to 3 were also formulated into a rinse-off shampoo formulation. Appropriate amounts of each Microcapsule Sample were formulated into 90.0 g of various shampoo formulations described in Tables 11, 12, and 13 to deliver a scent perfume oil usage level of 0.6 weight percent. Each Microcapsule Sample was added with water on top of the shampoo formulation and then mixed using a Speed-Mixer by Hauschild DAC 400FVZ mixer, at 1,850 RPM for 1 minute.

TABLE 11

| | EXAMPLE | | |
|---|---|---|---|
| Ingredient | 14A (wt %) | 14B (wt %) | 14C (wt %) |
| Water | QS | QS | QS |
| Polyquaternium 76 [1] | 2.50 | — | — |
| Guar, Hydroxypropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsule | 2.8 | 2.8 | 2.8 |
| Preservatives, pH adjustment | 1 | 1 | 1 |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW – 500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

TABLE 12

| Ingredient | 14D (wt %) | 14E (wt %) | 14F (wt %) |
|---|---|---|---|
| Water | QS | QS | QS |
| Silicone A[1] | 1.0 | — | — |
| Silicone B[2] | — | 0.5 | — |
| Silicone C[3] | — | — | 0.5 |
| Cyclopentasiloxane[4] | — | 0.61 | 1.5 |
| Behenyl trimethyl ammonium chloride[5] | 2.25 | 2.25 | 2.25 |
| Isopropyl alcohol | 0.60 | 0.60 | 0.60 |
| Cetyl alcohol[6] | 1.86 | 1.86 | 1.86 |
| Stearyl alcohol[7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone[8] | 0.0005 | 0.0005 | 0.0005 |
| Panthenol[9] | 0.10 | 0.10 | 0.10 |
| Panthenyl ethyl ether[10] | 0.05 | 0.05 | 0.05 |
| Fragrance | 0.35 | 0.35 | 0.35 |
| Fragrance Microcapsules | 2.8 | 2.8 | 2.8 |

[1]Glycidol Silicone VC2231-193
[2]Glycidol Silicone VC2231-193F
[3]Glycidol Silicone VC2231-193A
[4]Cyclopentasiloxane: SF1202 available from Momentive Performance Chemicals
[5]Behenyl trimethyl ammonium chloride/Isoproyl alcohol: Genamin™ KMP available from Clariant
[6]Cetyl alcohol: Konol™ series available from Shin Nihon Rika
[7]Steraryl alcohol: Konol™ series available from Shin Nihon Rika
[8]Methylchloroisothiazolinone/Methylisothiazolinone: Kathon TM CG available from Rohm & Haas
[9]Panthenol: Available from Roche
[10]Panthenyl ethyl ether: Available from Roche

TABLE 13

| Ingredient | 14G (wt %) | 14H (wt %) | 14I (wt %) | 14J (wt %) |
|---|---|---|---|---|
| Sodium Laureth Sulfate | 10.00 | 10.00 | 10.00 | 10.00 |
| Sodium Lauryl Sulfate | 1.50 | 1.50 | 1.50 | 1.50 |
| Cocoamidopropyl betaine | 2.00 | 2.00 | 2.00 | 2.00 |
| Guar Hydroxypropyl trimonium chloride (1) | 0.40 | | 0.40 | |
| Guar Hydroxypropyl trimonium chloride (2) | | 0.40 | | 0.40 |
| Dimethicone (3) | 2.00 | 2.00 | 2.00 | 2.00 |
| Gel Network (4) | | 27.27 | | 27.27 |
| Ethylene Glycol Distearate | 1.50 | 1.50 | 1.50 | 1.50 |
| 5-Chloro-2-methyl-4-isothiazolin-3-one, Kathon CG | 0.0005 | 0.0005 | 0.0005 | 0.0005 |
| Sodium Benzoate | 0.25 | 0.25 | 0.25 | 0.25 |
| Disodium EDTA | 0.13 | 0.13 | 0.13 | 0.13 |
| Perfume | 0.70 | 0.70 | 0.70 | 0.70 |
| Fragrance Microcapsules | 2.8 | 2.8 | 2.8 | 2.8 |
| Citric Acid/Sodium Citrate Dihydrate | pH QS | pH QS | pH QS | pH QS |
| Sodium Chloride/ Ammonium Xylene Sulfonate | Visc. QS | Visc. QS | Visc. QS | Visc. QS |
| Water | QS | QS | QS | QS |

(1) Jaguar C17 available from Rhodia
(2) N-Hance 3269 (with Mol. W. of ~500,000 and 0.8 meq/g) available from Aqualon/Hercules
(3) Viscasil 330M available from General Electric Silicones
(4) Gel Networks; See Composition below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

| Sample Gel Network | |
|---|---|
| Ingredient | Wt. % |
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 15

Additional microcapsule samples were produced using a spray drying process. The microcapsule samples were formed from the following solutions:

Solution A: 14.987 g phosphate ester PA-900 (obtained from Lakeland Chemical Ltd.) and 85 g Apple Bloom Mod 5 fragrance oil.

Solution B: 625.353 g of HICAP 100 starch (obtained from Ingredion) and 1,878 g water heated to 70° C.

Solution C: 75.68 g chitosan (obtained as TCI C2395 from TCI America) and 2,425 g deionized water.

Solution D: 360.69 g epomin P-1050 (50% aqueous solution of Polyethylenimine obtained from Nippon Shokubai Co. Ltd) and 1439.48 g deionized water.

Solution E: 10 g calcium chloride dehydrate and 90 g deionized water.

Microcapsule Sample 4 was produced by adding 10.033 g of Solution A to 240.14 g of Solution B while mixing at 760 RPM using a pitched blade turbine agitator for 1 minute. 1000.26 g of Solution C was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Microcapsule Sample 4 was produced by adding 10.033 g of Solution A to 240.14 g of Solution B while mixing at 760 RPM using a pitched blade turbine agitator for 1 minute. 1000.26 g of Solution C was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Microcapsule Sample 5 was produced by adding 10.012 g of Solution A to 240.08 g of Solution B while mixing at 760 RPM using a pitched blade turbine agitator for 1 minute. 300 g of Solution D was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Microcapsule Sample 6 was produced by adding 10.03 g of Solution A to 230.35 g of Solution B while mixing at 760 RPM using a pitched blade turbine agitator for 1 minute. 998.59 g of Solution C was then added at the same agitation for 1 minute. Finally, 25.147 g of Solution E was added at the same agitation and mixed for one minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Microcapsule Sample 7 was produced by adding 10.051 g of Solution A to 230.06 g of Solution B while mixing at 760 RPM using a pitched blade turbine agitator for 1 minute.

300 g of Solution D was then added at the same agitation for 1 minute. Finally, 25.08 g of Solution E was added at the same agitation and mixed for one minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Microcapsule Sample 8 was produced by adding 20.012 g of Solution A to 720.1 g of Solution B while mixing at 760 RPM using a pitched blade turbine agitator for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

Microcapsule Sample 9 was produced by adding 15.53 g of Solution A to 542 g of Solution B while mixing at 760 RPM using a pitched blade turbine agitator for 1 minute. 39.08 g of Solution E was then added at the same agitation for 1 minute. The resulting slurry was spray dried using a co-current Niro A/S dryer with a diameter of 3 feet and an inlet air temperature 200° C. and an outlet air temperature of 100° C., a dryer vacuum of −230 millimeters of water, and centrifugal wheel atomization at 5.0 bar.

The weight percentages of Microcapsules Samples 4 to 9 are depicted in Table 14. Microcapsule Sample I is comparative because it does not include a multivalent ion to cause precipitation of the phosphate ester and did not form stable microcapsules.

TABLE 14

| Material | Microcapsule Sample # | | | | | |
| --- | --- | --- | --- | --- | --- | --- |
|  | 4 | 5 | 6 | 7 | 8 | 9 |
| Fragrance Oil | 8.50% | 8.50% | 8.50% | 8.50% | 8.50% | 8.50% |
| Phosphate Ester PA-900 | 1.50% | 1.50% | 1.50% | 1.50% | 1.50% | 1.50% |
| HICAP 100 Starch | 60.00% | 60.00% | 57.50% | 57.50% | 90.00% | 87.50% |
| Chitosan | 30.00% | 0.00% | 30.00% | 0.00% | 0.00% | 0.00% |
| Epomin P Polyethyleneimine | 0.00% | 30.00% | 0.00% | 30.00% | 0.00% | 0.00% |
| Calcium Chloride | 0.00% | 0.00% | 2.50% | 2.50% | 0.00% | 2.50% |
| Water | 0.00% | 0.00% | 0.00% | 0.00% | 0.00% | 0.00% |

Microcapsule Samples 4 to 7 and 9 were also examined using microscopy.

Microcapsule Sample 4: A very thin membrane was observed in the few smooth morphology particles that had cracks. Wrinkled particles had a much higher nitrogen content (indicating there is a higher fraction of chitosan in this morphology). Small areas were found having a high local concentration of phosphate.

Microcapsule Sample 5: A more uniform morphology was observed with only one type of particle. All particles were slightly wrinkled. Overall, the microcapsules were more spherical in nature. Traditional matrix type of morphology was observed (wall of the particle has droplets surrounded by a matrix of polymer). Polyethyleniminecontent is high in the matrix capsule.

Microcapsule Sample 6: A very thin membrane was observed in the few smooth morphology particles that had cracks. A considerable number of fractured particles were observed in this sample. The fractured particles primarily exhibited a smooth morphology.

Microcapsule Sample 7: Two different types of morphology were observed—wrinkled and smooth. The particle size of the two morphologies were similar. Fractured capsules had high levels of calcium and phosphate. Nitrogen surrounds almost all of the particles, indicating the presence of polyethyleneimine.

Microcapsule Sample 9: Both smooth and wrinkled morphologies were observed. Some of the smooth morphology capsules were more brittle. Smooth morphology particles were larger in size than the wrinkled particles. There are many more wrinkled particles vs. smooth particles (80:20).

Microcapsule Samples 4 to 9 were included in the leave-on conditioner matrix of Example 14. The formulations of the leave-on conditioner are depicted in Table 15.

TABLE 15

| EXAMPLE | Microcapsules Description | Leave-on Conditioner Matrix (g) | Perfume or Microcapsule Sample (g) | Water (g) |
| --- | --- | --- | --- | --- |
| 15-1 | Control - Perfume Oil | 22.642 | 0.229 | 2.057 |
| 15-2 | Microcapsule Sample 4 | 22.636 | 2.241 | — |
| 15-3 | Microcapsule Sample 5 | 22.662 | 2.324 | — |
| 15-4 | Microcapsule Sample 6 | 22.644 | 2.302 | — |
| 15-5 | Microcapsule Sample 7 | 22.641 | 2.31 | — |
| 15-6 | Microcapsule Sample 8 | 22.645 | 2.349 | — |
| 15-7 | Microcapsule Sample 9 | 22.642 | 2.359 | — |

The Hair Switch Treatment method was used to apply the leave-on conditioner products onto hair. The hair was allowed to dry at ambient temperatures. After 4 hours, the hair switches were evaluated by 3 panelists. The results are depicted in Table 16 and FIG. 3.

TABLE 16

| Example | Microcapsule Sample | Description | Primavera Grade (4 hr) Pre-Comb/Post-Comb |
| --- | --- | --- | --- |
| 15-1 | Control - Perfume Oil | Control | 15/20 |
| 15-2 | Microcapsule Sample 4 | Starch/Chitosan/Perfume | 20/35 |
| 15-3 | Microcapsule Sample 5 | Starch/PE/Perfume | 20/45 |
| 15-4 | Microcapsule Sample 6 | Starch/Chitosan/CaCl$_2$/Perfume | 15/20 |
| 15-5 | Microcapsule Sample 7 | Starch/PEI/CaCl$_2$/Perfume | 20/25 |
| 15-6 | Microcapsule Sample 8 | Starch/Perfume | 20/35 |
| 15-7 | Microcapsule Sample 9 | Starch/Perfume/CaCl$_2$ | 20/30 |

Figure 3:
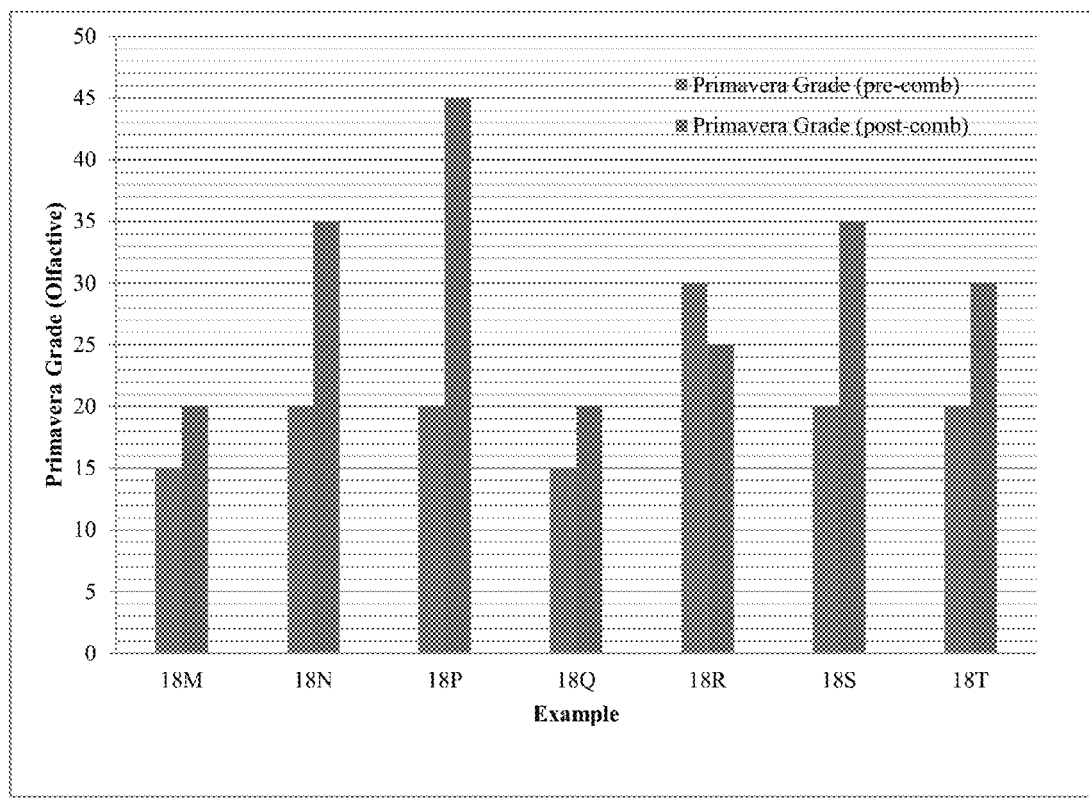
FIG. 3 depicts a bar chart of the fragrance intensity of various microcapsules on hair samples.

As depicted by Table 16 and FIG. 3, Comparative Example 15-1 formed without microcapsules does not result in a noticeable fragrance longevity in hair. Samples including the microcapsule samples, in contrast, exhibited improved fragrance release post-combing.

Example 16

The microcapsules of Example 15 can be incorporated into granular laundry detergent compositions depicted in Tables 17 and 18. The laundry detergent compositions can be used for hand washing or washing machines including top-loading washing machines. The typical pH of the laundry detergents can be about 10.

TABLE 17

|  | 16A (wt %) | 16B (wt %) | 16C (wt %) | 16D (wt %) | 16E (wt %) | 16F (wt %) |
| --- | --- | --- | --- | --- | --- | --- |
| Linear alkylbenzenesulfonate | 20 | 22 | 20 | 15 | 19.5 | 20 |
| $C_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.4 | 0.9 |
| AE7 | 0.0 | 0.0 | 0.0 | 1 | 0.1 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate ($SiO_2:Na_2O$ at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.05 | 0.0 |
| Carboxymethyl cellulose | 1 | 0.3 | 1 | 1 | 1 | 1 |
| Stainzyme ® (20 mg active/g) | 0.1 | 0.2 | 0.1 | 0.2 | 0.1 | 0.1 |
| Protease (Savinase ®, 32.89 mg active/g) | 0.1 | 0.1 | 0.1 | 0.1 |  | 0.1 |
| Amylase - Natalase ® (8.65 mg active/g) | 0.1 | 0.0 | 0.1 | 0.0 | 0.1 | 0.1 |
| Lipase - Lipex ® (18 mg active/g) | 0.03 | 0.07 | 0.3 | 0.1 | 0.07 | 0.4 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet Dye (DV9 or DV99 or DV66) | 0.0 | 0.0 | 0.0003 | 0.0001 | 0.0001 | 0.0 |
| Neat Perfume[1] | 0.5 | 0.5 | 0.5 | 0.5 | 0.5 | 0.5 |
| Microcapsules[2] | 0.7 | 1.0 | 2.3 | 0.5 | 1.2 | 0.8 |
| Sulfate/Moisture | Balance | | | | | |

[1]Optional.
[2]Microcapsules of Examples 15 (dry powders)

TABLE 18

|  | A (wt %) | B (wt %) | C (wt %) | D (wt %) | E (wt %) | F (wt %) |
| --- | --- | --- | --- | --- | --- | --- |
| Linear alkylbenzenesulfonate | 8 | 7.1 | 7 | 6.5 | 7.5 | 7.5 |
| AE3S | 0 | 4.8 | 1.0 | 5.2 | 4 | 4 |
| C12-14 Alkylsulfate | 1 | 0 | 1 | 0 | 0 | 0 |
| AE7 | 2.2 | 0 | 2.2 | 0 | 0 | 0 |
| $C_{10}$-12 Dimethyl hydroxyethylammonium chloride | 0.75 | 0.94 | 0.98 | 0.98 | 0 | 0 |
| Crystalline layered silicate (δ-$Na_2SiO_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R ($SiO_2:Na_2O$ at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease - Purafect ® (84 mg active/g) | 0.2 | 0.2 | 0.3 | 0.15 | 0.12 | 0.13 |
| Amylase - Stainzyme Plus ® (20 mg active/g) | 0.2 | 0.15 | 0.2 | 0.3 | 0.15 | 0.15 |
| Lipase - Lipex ® (18.00 mg active/g) | 0.05 | 0.15 | 0.1 | 0 | 0 | 0 |
| Amylase - Natalase ® (8.65 mg active/g) | 0.1 | 0.2 | 0 | 0 | 0.15 | 0.15 |

TABLE 18-continued

|  | A (wt %) | B (wt %) | C (wt %) | D (wt %) | E (wt %) | F (wt %) |
|---|---|---|---|---|---|---|
| Cellulase - Celluclean ™ (15.6 mg active/g) | 0 | 0 | 0 | 0 | 0.1 | 0.1 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |
| $MgSO_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |
| Neat Perfume[1] | 0.5 | 0.5 | 0.5 | 0.5 | 0.5 | 0.5 |
| Perfume Microcapsules[2] | 2.0 | 1.5 | 0.9 | 2.2 | 1.5 | 0.8 |
| Sulfate/Water & Miscellaneous | Balance | | | | | |

[1]Optional.
[2]Microcapsules of Examples 15

Example 18

The microcapsule samples of Example 15 can be incorporated into a heavy duty liquid detergent as depicted in Table 19.

TABLE 19

|  | A (wt %) | B (wt %) | C (wt %) | D (wt %) | E (wt %) | F (wt %) | G (wt %) |
|---|---|---|---|---|---|---|---|
| AES $C_{12-15}$ alkyl ethoxy (1.8) sulfate | 11 | 10 | 4 | 6.32 | 0 | 0 | 0 |
| AE3S | 0 | 0 | 0 | 0 | 2.4 | 0 | 0 |
| Linear alkyl benzene sulfonate/sulfonic acid | 1.4 | 4 | 8 | 3.3 | 5 | 8 | 19 |
| HSAS | 3 | 5.1 | 3 | 0 | 0 | 0 | 0 |
| Sodium formate | 1.6 | 0.09 | 1.2 | 0.04 | 1.6 | 1.2 | 0.2 |
| Sodium hydroxide | 2.3 | 3.8 | 1.7 | 1.9 | 1.7 | 2.5 | 2.3 |
| Monoethanolamine | 1.4 | 1.49 | 1.0 | 0.7 | 0 | 0 | To pH 8.2 |
| Diethylene glycol | 5.5 | 0.0 | 4.1 | 0.0 | 0 | 0 | 0 |
| AE9 | 0.4 | 0.6 | 0.3 | 0.3 | 0 | 0 | 0 |
| AE8 | 0 | 0 | 0 | 0 | 0 | 0 | 20.0 |
| AE7 | 0 | 0 | 0 | 0 | 2.4 | 6 | 0 |
| Chelant (HEDP) | 0.15 | 0.15 | 0.11 | 0.07 | 0.5 | 0.11 | 0.8 |
| Citric Acid | 2.5 | 3.96 | 1.88 | 1.98 | 0.9 | 2.5 | 0.6 |
| $C_{12-14}$ dimethyl Amine Oxide | 0.3 | 0.73 | 0.23 | 0.37 | 0 | 0 | 0 |
| $C_{12-18}$ Fatty Acid | 0.8 | 1.9 | 0.6 | 0.99 | 1.2 | 0 | 15.0 |
| 4-formyl-phenylboronic acid | 0 | 0 | 0 | 0 | 0.05 | 0.02 | 0.01 |
| Borax | 1.43 | 1.5 | 1.1 | 0.75 | 0 | 1.07 | 0 |
| Ethanol | 1.54 | 1.77 | 1.15 | 0.89 | 0 | 3 | 7 |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | 0.1 | 0 | 0 | 0 | 0 | 0 | 2.0 |
| Ethoxylated ($EO_{15}$) tetraethylene pentamine | 0.3 | 0.33 | 0.23 | 0.17 | 0.0 | 0.0 | 0 |
| Ethoxylated Polyethylenimine | 0 | 0 | 0 | 0 | 0 | 0 | 0.8 |
| Ethoxylated hexamethylene diamine | 0.8 | 0.81 | 0.6 | 0.4 | 1 | 1 |  |
| 1,2-Propanediol | 0.0 | 6.6 | 0.0 | 3.3 | 0.5 | 2 | 8.0 |
| Fluorescent Brightener | 0.2 | 0.1 | 0.05 | 0.3 | 0.15 | 0.3 | 0.2 |
| Hydrogenated castor oil derivative structurant | 0.1 | 0 | 0 | 0 | 0 | 0 | 0.1 |
| Perfume | 1.6 | 1.1 | 1.0 | 0.8 | 0.9 | 1.5 | 1.6 |
| Protease (40.6 mg active/g) | 0.8 | 0.6 | 0.7 | 0.9 | 0.7 | 0.6 | 1.5 |

TABLE 19-continued

|  | A (wt %) | B (wt %) | C (wt %) | D (wt %) | E (wt %) | F (wt %) | G (wt %) |
| --- | --- | --- | --- | --- | --- | --- | --- |
| Mannanase: Mannaway ® (25 mg active/g) | 0.07 | 0.05 | 0.045 | 0.06 | 0.04 | 0.045 | 0.1 |
| Amylase: Stainzyme ® (15 mg active/g) | 0.3 | 0 | 0.3 | 0.1 | 0 | 0.4 | 0.1 |
| Amylase: Natalase ® (29 mg active/g) | 0 | 0.2 | 0.1 | 0.15 | 0.07 | 0 | 0.1 |
| Xyloglucanase (Whitezyme ®, 20 mg active/g) | 0.2 | 0.1 | 0 | 0 | 0.05 | 0.05 | 0.2 |
| Lipex ® (18 mg active/g) | 0.4 | 0.2 | 0.3 | 0.1 | 0.2 | 0 | 0 |
| Neat Perfume[1] | 0.5 | 0.5 | 0.5 | 0.5 | 0.5 | 0.5 | 0.5 |
| Perfume Microcapsules[2] | 0.25 | 3.2 | 2.5 | 4.0 | 2.5 | 1.4 | 0.8 |
| *Water, dyes & minors |  |  |  | Balance |  |  |  |

*Based on total cleaning and/or treatment composition weight, a total of no more than 12% water
[1]Optional.
[2]Microcapsules of Examples 15.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The foregoing description of examples has been presented for purposes of description. It is not intended to be exhaustive or limiting to the forms described. Numerous modifications are possible in light of the above teachings. Some of those modifications have been discussed and others will be understood by those skilled in the art. The examples were chosen and described for illustration of various embodiments. The scope is, of course, not limited to the examples or embodiments set forth herein, but can be employed in any number of applications and equivalent articles by those of ordinary skill in the art. Rather it is hereby intended the scope be defined by the claims appended hereto.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A microcapsule comprising:
   a core material miscible with a lipophilic phosphate ester; and
   a shell wall at least partially surrounding the core material, the shell wall comprising the reaction product of the lipophilic phosphate ester and a multivalent ion.

2. The microcapsule of claim 1, wherein the core material has a C log P value of about 0 or greater.

3. The microcapsule of claim 1, wherein the core material comprises perfume oil.

4. The microcapsule of claim 1, wherein the core material is polar.

5. The microcapsule of claim 1 is encapsulated in a starch matrix.

6. The microcapsule of claim 5, wherein the starch matrix comprises an octenylsuccinic acid anhydride modified starch.

7. The microcapsule of claim 1, wherein the lipophilic phosphate ester comprises a phosphate alcohol ester.

8. The microcapsule of claim 7, wherein the phosphate alcohol ester has a carbon chain length between about 6 carbon atoms and about 18 carbon atoms.

9. The microcapsule of claim 1, wherein the lipophilic phosphate ester comprises a phosphate diester.

10. The microcapsule of claim 1, wherein the lipophilic phosphate ester has an acid value of about 180 mg KOH/g phosphate ester to about 450 mg KOH/g phosphate ester.

11. The microcapsule of claim 1, wherein the multivalent ion comprises one or more of aluminum sulfate, chitosan, polyethyleneimine, and polydiallyldimethylammonium chloride.

12. A composition comprising:
    an adjunct ingredient; and
    one or more microcapsules, wherein each of the one or more microcapsules comprises:
    a core material miscible with a lipophilic phosphate ester; and
    a shell wall comprising the reaction product of the lipophilic phosphate ester and a multivalent ion.

13. The composition of claim 12, wherein the core material has a C log P value of about 0 to about 5.

14. The composition of claim 13, wherein the core material comprises a perfume.

15. The composition of claim 14, wherein the lipophilic phosphate ester comprises a phosphate diester.

16. The composition of claim 15, wherein the lipophilic phosphate ester has an acid value of about 180 mg KOH/g phosphate ester to about 450 mg KOH/g phosphate ester.

17. The composition of claim 16, wherein the multivalent ion comprises one or more of aluminum sulfate, chitosan, polyethyleneimine, and polydiallyldimethylammonium chloride.

18. The composition of claim 17, wherein the adjunct ingredient comprises an antiperspirant active.

19. The composition of claim 17, wherein at least some of the microcapsules are encapsulated in a starch matrix.

20. The composition of claim 18, wherein the starch matrix comprises an octenylsuccinic acid anhydride modified starch.

\* \* \* \* \*